(12) United States Patent
Lafont

(10) Patent No.: US 11,865,156 B2
(45) Date of Patent: Jan. 9, 2024

(54) TREATMENT OF TOBACCO ADDICTION BY A TOBACCO LEAF EXTRACT

(71) Applicant: NFL Biosciences, Paris (FR)

(72) Inventor: Bruno Lafont, Ornex (FR)

(73) Assignee: NFL Biosciences, Castelnau-le-Lez (FR)

( * ) Notice: Subject to any disclaimer, the term of this patent is extended or adjusted under 35 U.S.C. 154(b) by 19 days.

(21) Appl. No.: 17/474,952

(22) Filed: Sep. 14, 2021

(65) Prior Publication Data
US 2021/0401921 A1 Dec. 30, 2021

Related U.S. Application Data

(63) Continuation of application No. 16/091,676, filed as application No. PCT/EP2017/058398 on Apr. 7, 2017, now Pat. No. 11,123,395.

(30) Foreign Application Priority Data

Apr. 7, 2016 (FR) ...................................... 1653079

(51) Int. Cl.
| | | |
|---|---|---|
| A61K 36/81 | (2006.01) | |
| A61K 9/00 | (2006.01) | |
| A61K 9/19 | (2006.01) | |
| A61P 25/34 | (2006.01) | |
| A61P 25/36 | (2006.01) | |

(52) U.S. Cl.
CPC ............ *A61K 36/81* (2013.01); *A61K 9/0019* (2013.01); *A61K 9/19* (2013.01); *A61P 25/34* (2018.01); *A61P 25/36* (2018.01); *A61K 2236/15* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 5,770,698 A | 6/1998 | Berrens | |
| 9,061,052 B2 * | 6/2015 | Nicolas | A61K 36/81 |
| 11,123,395 B2 * | 9/2021 | Lafont | A61P 25/36 |
| 2005/0250736 A1 * | 11/2005 | Cherkassky | A61K 9/0056 |
| | | | 424/48 |
| 2009/0162403 A1 | 6/2009 | Jacobi et al. | |
| 2011/0151035 A1 | 6/2011 | Wright, IV | |
| 2014/0343254 A1 | 11/2014 | Gerardi et al. | |

FOREIGN PATENT DOCUMENTS

| | | |
|---|---|---|
| CN | 101085104 | 12/2007 |
| CN | 104151140 | 11/2014 |
| WO | WO 2007/128924 | 11/2007 |

OTHER PUBLICATIONS

Andersen et al., *Chemical Composition of Tobacco Leaves Altered by Near-Ultraviolet and Intensity of Visible Light*, 51 Plant Physiol. 723-726 (1973).
Butorac et al., *The Effect of Tobacco Monoculture and Crop Rotations on Tobacco Leaf Composition*, 69 Agriculturae Conspectus Scientificus 95-101 (2004).
Leffingwell et al., *Basic Chemical Constituents of Tobacco Leaf and Differences among Tobacco Types*, Chapter 8 Production, Chemistry, and Technology 265-283 (1999).
Leffingwell, *Chemical Constituents of Tobacco Leaf and Differences Among Tobacco Types*, 1(12) Leffingwell Reports 1-56 (Feb. 2001).
Tang et al., *Yield and Nicotine Content of Flue-Cured Tobacco as Affected by Soil Nitrogen Mineralization*, 18(2) Pedosphere 227-235 (2008).
Wagner et al., *Variation in Cadmium Accumulation Potential and Tissue Distribution of Cadmium in Tobacco*, 82 Plant Physiol. 274-279 (1986).
*IARC Monographs on the Evaluation of Carcinogenic Risks to Human*, 89 World Health Organization International Agency for Research on Cancer (2007).
Edreva et al., *Pathogenesis-Related Proteins: Research Progress in the Last 15 Years*, 31(1-2) Gen. Appl. Plant. Physiology 105-124 (2005).
Fan et al., *Characteristics of plant proteinase inhibitors and their applications in combating phytophagous insects*, 46 Bot. Bull. Acad. Sin. 273-292 (2005).
Guevara-Morato et al., *Characterization of a pathogenesis-related protein 4 (PR-4) induced in Capsicum chinense $L^3$ plants with dual RNase and DNase activities*, 61(12) Journal of Experimental Botany 3259-3271 (2010).
Kim et al., *Protease Inhibitors from Plants with Antimicrobial Activity*, 10 Int. J. Mol. Sci. 2860-2872 (2009).
Lawrence et al., *Plant protease inhibitors in control of phytophagous insects*, 5(1) Electronic Journal of Biotechnology 93-109 (published Apr. 15, 2002).
Page extracted from the website "clinical trials.gov," which shows details of a Phase II clinical trial in progress with the tobacco leaf extract as claimed (called "CESTO2") (first posted Sep. 30, 2020; Last Updated Jan. 20, 2021; Printout from Mar. 17, 2021).
Authorization from the French National Agency for the Safety of Medicines & Health Products ("ANSM") regarding this Phase II clinical trial (original in French and English translation) (May 12, 2020).
Poster presented by the inventor Mr. Lafont at several renowned scientific meetings in the field, including at the 2019 annual meeting of the Society for Research on Nicotine and Tobacco ("SRNT") (2019).

(Continued)

*Primary Examiner* — Russell G Fiebig
(74) *Attorney, Agent, or Firm* — Panitch Schwarze Belisario & Nadel LLP; Erin M. Dunston

(57) ABSTRACT

The invention relates to a tobacco leaf extract containing, relative to the total weight of the extract, at least 5 wt.-% proteins essentially free of molecules with a molecular mass of less than 10 kDa. The invention also relates to a pharmaceutical composition containing such an extract and to the use thereof in the treatment of tobacco addiction.

14 Claims, 11 Drawing Sheets

(56) References Cited

OTHER PUBLICATIONS

First prize received for poster by the inventor Mr. Lafont at several renowned scientific meetings in the field, including at the 2019 annual meeting of the Society for Research on Nicotine and Tobacco ("SRNT") (2019).
Kbis extract (French and English versions) (Dec. 6, 2019).

* cited by examiner

TREATMENT OF TOBACCO ADDICTION BY A TOBACCO LEAF EXTRACT

CROSS-REFERENCE TO RELATED APPLICATIONS

This application is a U.S. Continuation Application of U.S. patent application Ser. No. 16/091,676, filed on Oct. 5, 2018, now U.S. Pat. No. 11,123,395, issued on Sep. 21, 2021, which is a U.S. National Stage Application pursuant to 35 U.S.C. § 371 of International Patent Application PCT/EP2017/058398, filed on Apr. 7, 2017, and published as WO 2017/174787 on Oct. 12, 2017, which claims priority to French Patent Application 1653079, filed on Apr. 7, 2016, all of which are incorporated herein by reference in their entireties for all purposes.

FIELD OF THE INVENTION

The present invention concerns a tobacco leaf extract, as well as a pharmaceutical composition containing this tobacco leaf extract and the use thereof in the treatment of tobacco addiction.

PRIOR ART

In general, dependence or addiction has been defined by the World Health Organization as "a syndrome for which the use of a substance takes on a much higher priority than other behaviours that once had greater value. In its extreme form, the state of dependence is characterized by an irresistible need for a substance that compels the individual suffering from this dependence to impulsively seek this substance".

Tobacco dependence causes major public health problems, with a large number of smoking-related diseases such as cancer (lung, throat, mouth, lips, etc.), cardiovascular diseases, chronic bronchitis, etc. In addition to the diseases themselves, smoking has many side effects (decreased fertility, alteration of the epidermis, alteration of the oral and nasal mucosa, alteration of the cerebral arteries, damage to the oesophagus and stomach, vitamin B and C deficiencies, etc.).

There are three types of tobacco dependence which act concomitantly: physical dependence which is essentially due to the presence of nicotine in tobacco and which is expressed as a feeling of craving (strong urge to smoke, irritability, nervousness, restlessness, anxiety, sleep disturbance, etc.); psychological dependence which is linked to the psychoactive effects of nicotine which provides pleasure, relaxation, intellectual stimulation, anxiolytic, antidepressant and appetite suppressant action; and environmental or behavioural dependence which depends on social and friendly pressure. Physical dependence disappears on average in a few weeks. Withdrawal symptoms peak around three to four days after quitting smoking and may last several weeks. Psychological dependence takes longer to diminish and can last several months.

Tobacco dependence is maintained through positive and negative reinforcements. Nicotine is responsible for the release of dopamine, a neurotransmitter in the reward circuit. The smoker smokes both to reproduce the feelings of pleasure caused by the release of dopamine (this is the positive reinforcement of the cigarette) and to avoid withdrawal symptoms when his dopamine level is too low (this is the negative reinforcement of the cigarette).

There are three main methods of pharmacological treatment of tobacco dependence. The first aims at immediate cessation as of a target quit date initially set, with pharmacological treatments administered after this target quit date in the case of nicotine substitutes and one week before in the case of bupropion or varenicline (in order to reach a sufficient plasma concentration at the time of the target quit date). The second consists in reducing his consumption before an attempt to stop, in which the reduction phase corresponds to a pre-treatment during which pharmacological treatments are administered. The third is relapse prevention after successful cessation. To these three methods can be added cutting down without attempting to stop.

The efficacy of each of these methods is reinforced by a preparation phase for the smoker, who must convince himself of the need to stop smoking and to reinforce his motivation to do so. The prescribing information for pharmacological treatments for tobacco dependence thus indicate that smoking cessation treatments are more likely to be successful in patients who are motivated to quit smoking.

There are currently four main types of treatment for tobacco dependence (not to mention behavioural psychotherapies, acupuncture and hypnosis), namely nicotine substitutes, bupropion, varenicline and homeopathy. The principle of action of each of these four methods is based on the fact that nicotine is the molecule responsible for the mechanism of tobacco dependence.

Nicotine substitutes can be administered in a variety of ways: transdermally in the form of patches, orally in the form of chewing gum, lozenges or sublingual tablets, or via the pulmonary route in the form of inhalers. The administration of nicotine substitutes chiefly allows the reduction of the negative reinforcements of the cigarette by preventing as much as possible the smoker from feeling the withdrawal symptoms related to cessation, with the nicotine provided by the substitutes compensating for that of the cigarettes. The efficacy of nicotine substitutes varies according to the method used, with cessation rates generally ranging from 15 to 20%. Nicotine substitutes are used during attempts at immediate cessation and also as pre-treatment before cessation attempts to help smokers reduce their cigarette consumption as part of a gradual cessation (cut down to quit). They can also be used for the sole purpose of reducing tobacco consumption. Their efficacy in preventing relapse has not yet been demonstrated.

Bupropion, marketed by GlaxoSmithKline Laboratories (under the brand name Zyban®), acts on certain brain neurotransmitters such as catecholamines, noradrenaline and dopamine. Bupropion is a selective catecholamine reuptake inhibitor, which gives it antidepressant properties. Its efficacy is equivalent to that obtained after the use of nicotine patches (cessation rate around 20%). It is prescribed less than nicotine substitutes because it has a lower benefit/risk ratio for comparable efficacy. Indeed, it can lead to suicide attempts.

Varenicline, marketed by Pfizer Laboratories (under the brand name Chantix® or Champix®), is a partial agonist of nicotinic acetylcholine receptors. Varenicline targets these receptors with a dual action: an α4ß2 receptor partial agonist, it produces a reaction similar to that induced by nicotine with a lower intensity (and thus reduces craving effects during withdrawal); and at the beginning of treatment, when the smoker is treated while smoking occasionally, it attenuates neurochemical stimulation in the presence of nicotine (α4ß2 receptor partial antagonist). Varenicline thus reduces the negative (withdrawal effect) and positive (urge to smoke) reinforcements of cigarettes. In practice, varenicline reduces the pleasure of smoking, which would be a criterion for future success in quitting smoking. Its efficacy is greater than that of nicotine substitutes (cessation rate of about 28%). Varenicline is used for immediate cessation attempts and also as pre-treatment for a few weeks prior to cessation attempts to help smokers reduce their cigarette consumption as part of a gradual cessation (cut down to quit). In a first study (NCT00789074), 35% of smokers were able to reduce their cigarette consumption by at least 50% according to a point made after 3 weeks of pre-treatment with varenicline. In a second study (NCT00835900), the percentage reduction in the number of cigarettes smoked according to a point made at 4 weeks pre-treatment with varenicline was 42%. In a third study (NCT01370356), 47% of smokers were able to reduce their cigarette consumption by at least 50% according to a point made after 4 weeks of pre-treatment with varenicline. Its efficacy in preventing relapse has not yet been demonstrated. However, varenicline induces frequent side effects (nausea) and may be the cause of heart problems or suicide attempts. These side effects mean that despite an efficacy superior to nicotine substitutes, varenicline is often prescribed only as second-line therapy after failure with nicotine substitutes.

The fourth cessation route is homeopathy, which is based on the use of infinitesimal doses of the substance causing the symptoms one wishes to control. An extract of "tabacum" is often used in smoking cessation. Irish patent application IE 960 511 notably describes the use of homeopathic dilutions of tobacco extract for the manufacture of a medicinal product intended for the restoration of neuronal functions and the relief of nicotine withdrawal symptoms. Like other unconventional cessation techniques, its efficacy is inadequate in heavy smokers.

Despite much research in this area, there is still a need to find new treatments or to improve existing treatments for tobacco dependence.

In application PCT/FR2007/000786, the Applicant discovered that giving a smoker an injection of an aqueous solution of extract of tobacco leaves made it possible to treat the tobacco dependence of said smoker. This discovery was truly unexpected because the Applicant was able to determine that said aqueous tobacco leaf extract contained small amounts of nicotine. Thus, the mechanism of action involved in the treatment of tobacco dependence using this aqueous tobacco leaf extract is not the supply of nicotine to the smoker.

However, the fact that said aqueous tobacco leaf extract contained small amounts of nicotine did not provide information about its composition and its method of manufacture. The nicotine content of aqueous tobacco leaf extracts can indeed vary considerably depending on many factors.

The nicotine content in tobacco leaves can vary from 0.5 to 8% for the principal types of tobacco grown (Davis et al., "Production, Chemistry, and Technology", ISBN-13: 978-0632047918, Chapter 8, page 275).

Burley tobacco contains about twice as much nicotine as Maryland tobacco and three times as much nicotine as Oriental tobacco (Leffingwell, "Chemical constituents of tobacco leaf and differences among tobacco types", Leffingwell Reports, Vol. 1 (No. 2), February, 2001).

The use of nitrogen fertilizers influences the nicotine content of tobacco leaves and the nicotine content is higher in the upper leaves than in the middle leaves, which in turn is higher than in the lower leaves (Xiao-Tang et al., "Yield and nicotine content of flue-cured tobacco as affected by soil nitrogen mineralization", Pedosphere 18(2): 227-235, 2008, ISSN 1002-0160/CN 32-1315/P).

Crop rotation influences the nicotine content of tobacco leaves (Butorac et al., "The Effect of Tobacco Monoculture and Crop Rotations on Tobacco Leaf Composition", Agriculturae Conspectus Scientificus, Vol. 69 (2004) No. 4 (95-101)).

The chemical composition and nicotine content of tobacco leaves are influenced by ultraviolet radiation and light intensity (Andersen et al., "Chemical composition of tobacco leaves altered by near-ultraviolet and intensity of visible light", Plant Physiol. (1973) 51, 723-726).

Extract preparation methods also influence nicotine content, particularly maceration times and conditions, sterilization methods, and physical and chemical separations.

A tobacco extract such as that described in application PCT/FR2007/000786 comprises molecules of low molecular mass, i.e. less than 10 kDa. These low molecular weight molecules include tobacco-specific N-nitrosamines (TSNA) and N-nitrosoamino acids derived from non-volatile alkaloids, volatile aldehydes, polynuclear aromatic hydrocarbons (such as benzo[a]pyrene), lactones, urethanes, or metals such as cadmium for example (see Wagner et al., Plant Physiol. 1986, 82, 274-279 and IARC Monographs on the Evaluation of Carcinogenic Risks to Human, vol. 49). These compounds can be carcinogenic, mutagenic or toxic and can cause cancer as well as kidney and bone problems. These compounds are thus harmful to the health of the patient to which a composition containing said compounds has been administered.

Such a tobacco extract comprises many proteins of all molecular weights. For example, the Swiss-Prot database identifies 759 tobacco proteins. The RuBisCO protein alone can represent 30 to 50% of soluble proteins. A complete RuBisCO protein typically has eight subunits forming a protein complex of about 540 kDa. The toxicity of these proteins administered subcutaneously in solution is unknown although there is no indication that all or some of them may be involved in any therapeutic effect.

The objective of the present invention is to provide effective treatment for tobacco addiction. Advantageously, this treatment is non-toxic, is well tolerated by patients, and presents a limited risk by reducing as much as possible the administration of molecules of unknown toxicity that do not in principle have a therapeutic effect.

Although tobacco extracts contain thousands of compounds, the Applicant surprisingly discovered that proteins from tobacco leaf extracts induce a specific IgG immune response that promotes smoking cessation. Thus, the tobacco leaf extract according to the invention comprising a high protein content and a particular protein composition induces a specific IgG immune response that promotes smoking cessation.

This discovery is all the more surprising as the aqueous tobacco leaf extracts contain thousands of compounds, with proteins constituting only one family of compounds among others. Tobacco proteins are not known to play a role in tobacco addiction and therefore there is no incentive to use them in smoking cessation.

The Applicant shows in particular that the tobacco leaf extracts according to the invention have a high protein content and a particular protein composition. This particular protein composition can be notably obtained when cured tobacco leaves are used. Curing promotes the degradation of proteins, for example through hydrolysis mechanisms, and the increase of free amino acids in tobacco leaves (Hamilton & Lowe, 1978; Long & Weybrew, 1981; Burton, et al., 1983).

The Applicant surprisingly discovered that proteins from tobacco leaf extracts according to the invention induce the generation of specific IgG antibodies that promote smoking cessation. The Applicant shows that the administration of the tobacco leaf extract according to the invention induces the specific IgG immune response and makes it possible to obtain effective treatment for tobacco addiction, even without adding to the extract adjuvant that can promote an immune response. The Applicant shows that the specific IgG immune response, the treatment of tobacco addiction, and smoking cessation are particularly effective when extracts of cured tobacco leaves are used.

This discovery is all the more surprising as there is nothing in the prior art to indicate that IgG antibodies specific to tobacco leaf extract proteins are likely to help smokers reduce or stop smoking. The activation of a specific IgG immune response following the administration of tobacco extracts and the role of tobacco extracts in smoking cessation have never been described to date. Such a link between the immune system (involved notably in the production of specific IgG antibodies) and the nervous system (involved notably in the perception of the act of smoking and behaviour) which can promote smoking cessation has never been described to date.

Advantageously, the treatment of tobacco addiction according to the present invention requires the administration of the pharmaceutical composition according to the invention only a few times, advantageously only one administration, so that the effects of the reinforcements of the cigarette are no longer felt or are felt significantly less by the patient, and in particular the urge to smoke (positive reinforcement) and the palatability of the cigarette is reduced.

SUMMARY OF THE INVENTION

In a first aspect, the present invention concerns a tobacco leaf extract containing at least 5% by weight, based on the total weight of the dry extract, of proteins of molecular mass greater than 10 kDa and essentially free of molecules of molecular mass less than 10 kDa. Preferably, said proteins are selected from the group consisting of the following protein families: lignin-forming anionic peroxidase, glucan endo-1,3-beta-glucosidase, endochitinase, pathogenesis-related protein, osmotin and proteinase inhibitor and mixtures thereof.

The invention further concerns a pharmaceutical composition comprising said tobacco leaf extract and the use thereof in the treatment of tobacco addiction.

The invention further concerns a pharmaceutical composition comprising said tobacco leaf extract and the use thereof in smoking cessation.

The invention further concerns a method for treating tobacco addiction comprising administering said tobacco leaf extract to a subject suffering from tobacco addiction or dependence.

The invention further concerns a method for treating tobacco addiction comprising administering said pharmaceutical composition comprising said tobacco leaf extract to a subject suffering from tobacco addiction.

In the context of the present invention, the treatment of tobacco dependence or addiction encompasses all forms of tobacco consumption, namely smoked tobacco, in the form of manufactured or rolled cigarettes, cigarillos or cigars, pipe tobacco, but also smokeless tobacco such as snuff, chewing tobacco or snus.

The invention also concerns the process for preparing said tobacco leaf extract containing at least 5% by weight, based on the total weight of the dry extract, of proteins of molecular mass greater than 10 kDa and essentially free of molecules of molecular mass less than 10 kDa, comprising the following steps:
a. Curing of tobacco leaves,
b. Grinding of cured tobacco leaves to obtain ground cured tobacco leaves,
c. Extraction of the ground cured tobacco leaves under mechanical stirring with a solvent, for example an aqueous solvent, preferably an aqueous buffer solution with a pH between 6.0 and 8.5,
d. Separation of solid residues from the ground cured tobacco leaf extract solution by filtration or centrifugation to obtain a solid residue-free ground cured tobacco leaf extract solution,
e. Constant-volume filtration of the solution obtained in step d with a solvent, preferably an aqueous solvent, in an amount ranging from 2 to 12 times by volume, preferably from 3 to 10 times by volume, preferably from 4 to 8 times by volume, preferably 6 times by volume, based on the volume of the extract, and with a 10 kDa cut-off membrane,
f. Optionally lyophilization of the protein solution obtained in step e.

The invention also concerns a kit comprising a pharmaceutical composition comprising said tobacco leaf extract containing at least 5% by weight, based on the total weight of the dry extract, of proteins of molecular mass greater than 10 kDa and essentially free of molecules of molecular mass less than 10 kDa.

DETAILED DESCRIPTION OF THE INVENTION

Tobacco Leaf Extract

Figure 1:
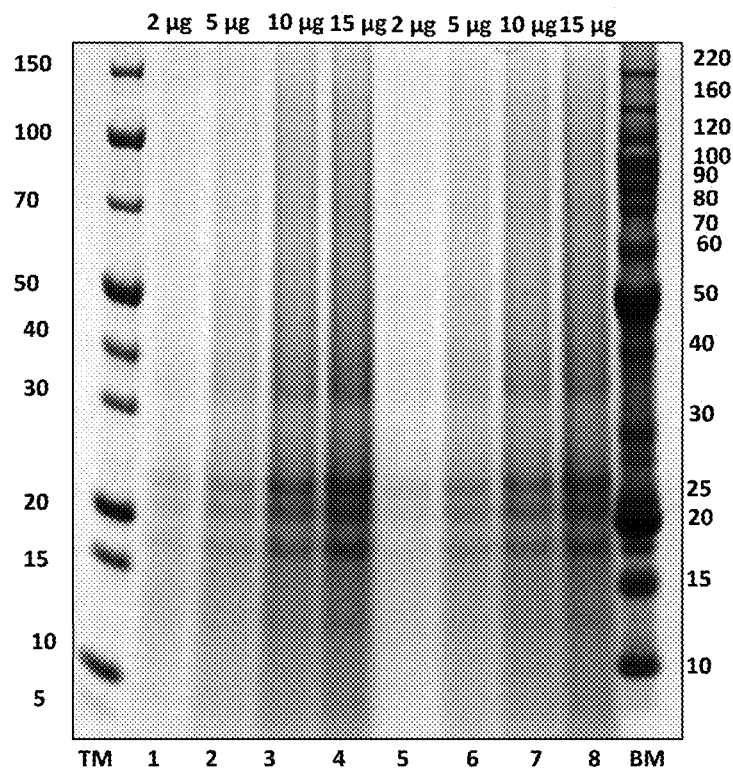
FIG. 1. Illustration of an electrophoretic profile of the tobacco leaf extract according to example 1: Fractionation on a 4%-12% NuPage gel in MES buffer and in the presence of reducing agent.

The present invention concerns a tobacco leaf extract containing at least 5% by weight, based on the total weight of the dry extract, preferably at least 10% by weight, preferably at least 15% by weight, preferably about 20% by weight of proteins of molecular mass greater than 10 kDa and essentially free of molecules of molecular mass less than 10 kDa.

The dry extract is advantageously obtained before lyophilization of the tobacco leaf extract according to the invention, then placed under a vacuum bell-jar, preferably in the presence of $P_2O_5$, until a constant mass of extract is obtained.

Advantageously, the content of molecules of molecular mass less than 10 kDa is less than 5% by weight based on the total weight of the extract, preferably less than 2.5% by weight, and better still less than 1% by weight.

For the purposes of the present invention, "about" means plus or minus 1% due to measurement uncertainties.

The content of proteins of molecular mass greater than 10 kDa usually measured in tobacco leaf extracts is about 1%. The tobacco leaf extract according to the present invention therefore has a content of proteins of molecular mass greater than 10 kDa which is much higher than previously known.

Preferably, the proteins present in the extract according to the present invention are chosen from the group consisting of the following protein families: lignin-forming anionic peroxidase, glucan endo-1,3-beta-glucosidase, endochitinase, pathogenesis-related protein, osmotin and proteinase inhibitor and mixtures thereof.

The names indicated for the proteins present in the extract according to the present invention correspond to the names given in the Swiss-Prot database, which is a biological database listing protein sequences.

According to one embodiment, the tobacco leaf extract according to the invention comprises at least one protein belonging to the family of glucan endo-1,3-beta-glucosidases, and preferably chosen from beta-1,3-endoglucanase acidic isoform PR-Q' (PR36401 according to the UniProt database), beta-1,3-endoglucanase basic vacuolar isoform GLB (P27666 according to the UniProt database), and mixtures thereof.

According to one embodiment, the tobacco leaf extract according to the invention comprises at least one protein belonging to the family of endochitinases, and preferably chosen from acidic endochitinase P (P17513 according to the UniProt database), acidic endochitinase Q (P17514 according to the UniProt database), endochitinase B (P24091 according to the UniProt database), and mixtures thereof.

According to one embodiment, the tobacco leaf extract according to the invention comprises at least osmotin (P14170 according to the UniProt database).

According to one embodiment, the tobacco leaf extract according to the invention comprises at least one lignin-forming anionic peroxidase (P11965 according to the UniProt database).

According to one embodiment, the tobacco leaf extract according to the invention comprises at least one pathogenesis-related protein, and preferably chosen from pathogenesis-related protein R (P13046 according to the UniProt database), pathogenesis-related protein PR-4A (PR29062 according to the UniProt database), pathogenesis-related protein PR-4B (PR29063 according to the UniProt database), and mixtures thereof.

According to one embodiment, the tobacco leaf extract according to the present invention comprises at least one protein belonging to the family of proteinase inhibitors, and preferably chosen from proteinase inhibitor I-B (Q03199 according to the UniProt database), proteinase inhibitor I-A (Q03198 according to the UniProt database), and mixtures thereof.

According to one embodiment, the tobacco leaf extract also comprises polysaccharides of molecular mass greater than 10 kDa and preferably water-soluble.

Preferably, the tobacco leaf extract according to the present invention comprises at least 5% by weight based on the total weight of the dry extract, preferably at least 10% by weight, preferably at least 15% by weight, preferably about 20% by weight of proteins selected from the group consisting of the following protein families: lignin-forming anionic peroxidase, glucan endo-1,3-beta-glucosidase, endochitinase, pathogenesis-related protein, osmotin and proteinase inhibitor and mixtures thereof.

According to one embodiment, the tobacco leaf extract according to the present invention is essentially free of high molecular mass proteins.

For the purposes of the present invention, "high molecular mass protein" means a protein whose molecular mass is greater than 500 kDa, preferably whose molecular mass is greater than 400 kDa, more preferably whose molecular mass is greater than 300 kDa, preferentially whose molecular mass is greater than 200 kDa, even more preferentially whose molecular mass is greater than 150 kDa, and better still whose molecular mass is greater than 100 kDa.

According to one embodiment, the tobacco leaf extract according to the present invention is essentially free of proteins whose molecular mass is greater than 50 kDa.

For the purposes of the present invention, "substantially free" means a content of molecules less than 15% by weight based on the total protein weight of the extract, preferably a content of molecules less than 10% by weight based on the total protein weight of the extract, more preferably less than 7.5% by weight based on the total protein weight of the extract, more preferably less than 5% by weight based on the total protein weight of the extract, preferentially less than 2.5% by weight based on the total protein weight of the extract, more preferentially less than 1% by weight based on the total protein weight of the extract, and better still less than 0.5% by weight based on the total protein weight of the extract.

Advantageously, the content of high molecular mass proteins is less than 15% by weight based on the total protein weight of the extract, preferably less than 10% by weight based on the total protein weight of the extract, more preferably less than 7.5% by weight based on the total protein weight of the extract, more preferably less than 5% by weight based on the total protein weight of the extract, preferentially less than 2.5% by weight based on the total protein weight of the extract, more preferentially less than 1% by weight based on the total protein weight of the extract, and better still less than 0.5% by weight based on the total protein weight of the extract.

According to one embodiment, the tobacco leaf extract according to the present invention is essentially free of RuBisCO proteins.

According to one embodiment, the tobacco leaves are of the variety *Nicotiana Tabacum* or the variety *Nicotiana Rustica*. The tobacco leaves may come from brown or blond tobacco and may be selected from Virginia tobacco, Burley tobacco, Oriental tobacco, Latakia tobacco, Perique tobacco, Maryland tobacco, Kentucky tobacco, California tobacco, Tex Mex tobacco, and mixtures thereof.

Of course, the extract does not necessarily consist of a pure extract of tobacco leaves, and proteins extracted from cannabis can be added to treat both tobacco and cannabis dependence.

According to a particular embodiment, the tobacco leaf extract is obtained from a 1/1/1 blend of brown tobacco, Virginia tobacco and Burley tobacco.

According to a particular embodiment, the tobacco leaf extract is obtained from Burley tobacco.

According to one embodiment, the tobacco leaf extract is obtained from cured tobacco leaves.

According to a particular embodiment, the tobacco leaf extract is obtained from air-cured tobacco leaves.

According to a particular embodiment, the tobacco leaf extract is obtained from tobacco leaves air-cured for a duration adapted to local climatic conditions, preferably for a minimum duration of one month.

For the purposes of the present invention, "air-curing" or "natural curing" means curing carried out in the presence of natural outdoor or indoor air. Air-curing can be carried out in an open or closed, covered or uncovered structure. Air-curing can for example be carried out in a natural curing barn. In this case, freshly harvested or pre-cured tobacco leaves are left to cure naturally under the effect of open air. The tobacco leaves can for example be hung in unheated ventilated barns. The tobacco leaves can for example be left to cure naturally until they turn brown. At this stage, there is practically no sugar left in the leaf. Advantageously, curing is carried out for a duration adapted to local climatic conditions, preferably for a minimum duration of one month. By way of example, curing can be carried out between September and December for harvests in central France. The tobacco leaves may be turned or aerated one or more times during curing, so as to allow uniform curing and to avoid the formation of condensation and the rotting or degradation of the leaves. The air-curing method can be used for example for Burley variety tobacco.

According to a particular embodiment, the extract of tobacco leaves is obtained from tobacco leaves cured in a natural curing barn.

According to another particular embodiment, the tobacco leaf extract is obtained from tobacco leaves cured in a heated curing barn. In this case, curing can be carried out in a barn or a structure heated to a suitable temperature.

According to another particular embodiment, the tobacco leaf extract is obtained from flue-cured tobacco leaves. In this case, curing can be carried out in a structure or a barn heated to a suitable temperature. Heat can be introduced into the structure or the barn through ducts connected to an external heat source. This controlled heating produces yellow-orange leaves. These leaves thus contain a high sugar content. Virginia tobacco can for example be cured according this method.

According to another particular embodiment, the tobacco leaf extract is obtained from sun-cured tobacco leaves. In this case, the tobacco leaves can be spread on racks and exposed to the sun for 12 to 30 days. Under direct light and heat from the sun, the leaves turn yellow or orange and retain a high sugar content. Oriental tobacco is generally cured using this method.

According to another particular embodiment, the tobacco leaf extract is obtained from fire-cured tobacco leaves. In this case, small pieces of wood can be burned beneath the tobacco leaves, which cure while absorbing a "smoky" aroma.

The tobacco leaf extract according to the present invention is advantageously an aqueous extract.

The tobacco leaf extract according to the present invention is advantageously an aqueous extract that is brown in colour.

Preferably, the tobacco leaf extract is obtainable by a solvent extraction process, for example an aqueous solvent, of ground cured tobacco leaves followed by separation of solid residues from the ground cured tobacco leaf extract solution then constant-volume diafiltration of the solid residue-free ground cured tobacco leaf extract solution with an aqueous solvent in an amount ranging from 2 to 12 times by volume, preferably 3 to 10 times by volume, preferably 4 to 8 times by volume, preferably 6 times by volume, based on the volume of the extract and with a 10 kDa cut-off membrane.

Of course, other types of solvent can be used to carry out the extraction process of the tobacco leaf extract. The extraction of step c can be carried out with an organic or inorganic solvent, or with a mixture of organic and/or inorganic solvents.

To ensure good extraction efficiency and yield, and to obtain an extract of good quality with the desired purity properties and composition, the skilled person will easily know how to select the appropriate solvent(s) according to the following criteria:
 the polarity of the solvent or solvent mixture (polar or non-polar);
 the physical state of the solvent or solvent mixture (for example liquid, solid, supercritical or gaseous);
 the chemical nature of the solvent or solvent mixture (for example organic or inorganic);
 the charge of the solvent or solvent mixture (for example ionic or non-ionic);
 the origin of the solvent or solvent mixture;
 the miscibility of the solvent or solvent mixture;
 the solubility of the solvent or solvent mixture.

The skilled person will know which technique to use to select the solvent(s) corresponding to his criteria, based on the desired extraction yield and extract purity and composition.

Advantageously, the tobacco leaf extract according to the present invention is obtained by the tobacco leaf preparation process described below.

Pharmaceutical Composition

In a second aspect, the present invention concerns a pharmaceutical composition comprising as active principle the tobacco leaf extract as described above.

The pharmaceutical composition according to the present invention further comprises at least one pharmaceutically acceptable excipient, such as pharmaceutically acceptable solvents, and for example water.

Advantageously, the pharmaceutical composition comprises proteins present in the tobacco leaf extract according to the invention in a content ranging from 1 to 1 000 µg/mL, preferably from 10 to 500 µg/mL, preferably from 50 to 300 µg/mL, preferably from 60 to 200 µg/mL, preferably between 80 and 150 µg/mL.

The pharmaceutical composition according to the invention is preferably an aqueous composition.

According to a particular embodiment, the pharmaceutical composition may further comprise an active agent acting on negative reinforcement, such as for example a nicotine substitute, varenicline or bupropion.

According to an embodiment, the pharmaceutical composition further comprises an adjuvant. Examples of adjuvants include swelling agents such as for example a sugar such as lactose, sucrose, trehalose, sorbitol, glucose, raffinose, mannitol, preferably lactose, sucrose, trehalose, glucose, or mannitol, an amino acid such as arginine, glycine or histidine, preferably glycine, or polymers of dextran or polyethylene glycol type, or mixtures thereof. According to this embodiment, the pharmaceutical composition comprises 50 to 99% by weight of adjuvants, preferably 80 to 97% by weight, based on the total weight of the pharmaceutical composition.

According to a particular embodiment, the pharmaceutical composition may further comprise proteins extracted from cannabis.

According to one embodiment, the pharmaceutical composition according to the present invention is provided in a form suitable for subcutaneous administration.

According to another embodiment, the pharmaceutical composition is provided in a form suitable for administration by means of an adhesive transdermal therapeutic system. Advantageously, the pharmaceutical composition is provided in patch form.

According to another embodiment, the pharmaceutical composition is provided in a form suitable for administration by spraying or by vaporization. Advantageously, the pharmaceutical composition is provided in sprayer, vaporizer or aerosol form.

The pharmaceutical composition according to the invention is preferably prepared according to the process for preparing a pharmaceutical composition comprising the tobacco leaf extract described below.

Use of the Pharmaceutical Composition

In a third aspect, the present invention concerns the use of the pharmaceutical composition for the treatment of tobacco addiction.

For the purposes of the present invention, "treatment of tobacco addiction" or "treatment of tobacco dependence" means more precisely the reduction of the addictive reinforcements of the cigarette. The administration of the pharmaceutical composition according to the invention notably reduces the positive reinforcements of the cigarette and in particular the urge to smoke.

The present invention also concerns a composition comprising a tobacco leaf extract as defined above for use in the treatment of tobacco addiction.

In other words, the present invention also concerns a method for treating tobacco addiction or dependence, comprising administering a composition comprising a tobacco leaf extract as defined above.

Advantageously, the administration of the composition according to the invention enables the patient to stop smoking, to decrease his consumption or to prevent his relapse after stopping by attenuating the positive reinforcements of tobacco and notably the urge to smoke, thus facilitating smoking cessation. Advantageously, the administration of the composition helps any type of smoker, i.e. including heavy smokers, to stop smoking and to decrease or avoid relapse after quitting.

Advantageously, the administration of the composition according to the invention further comprising proteins extracted from cannabis makes it possible to treat dependence or addiction to tobacco and cannabis at the same time.

According to one embodiment, the composition according to the present invention is administered by subcutaneous injection. According to this embodiment, the pharmaceutical composition is provided in a form suitable for subcutaneous administration.

According to one embodiment, the pharmaceutical composition is provided in a dosage form of 0.03 mL to 10 mL, preferably 0.1 mL to 5 mL, preferably 0.5 to 2 mL. The pharmaceutical composition is thus preferably administered in an amount of 0.03 mL to 10 mL, preferably 0.1 to 5 mL, preferably 0.5 mL to 2 mL by subcutaneous injection.

According to one embodiment, the composition according to the present invention is administered by means of an adhesive transdermal therapeutic system containing the tobacco leaf extract as defined above. According to this embodiment, the pharmaceutical composition is provided in a form suitable for administration by means of an adhesive transdermal therapeutic system. Advantageously, the pharmaceutical composition is provided in patch form.

The patch can be in the form of a reservoir-type patch with one or more compartments or a matrix-type patch. The practical execution of the patches will be determined by the skilled person based on his general knowledge of the subject to obtain a controlled and prolonged systemic administration of the tobacco leaf extract, over the entire period of application of the patch, for example for a duration of about 2 h to 24 h.

The reservoir-type patch will comprise one or more separate reservoir(s) containing the active principle(s) (including the tobacco leaf extract) in solution or suspended in the polymer matrix coming into contact with the skin via a semi-permeable polymeric membrane allowing the rate of release of the active principle(s) to be adjusted.

The matrix-type patch will comprise a polymeric mass within which the active principle(s) will be dissolved or dispersed in the appropriate proportions. These active principles are released by diffusion through the polymer chains of said matrix.

According to a particular embodiment of this type of patch, the adhesive covers the entire release surface of the matrix and is an integral part of the latter. This is therefore an active adhesive-type patch well known to the skilled person, which is of simplified manufacture and which allows the creation of thin, suitably flexible patches allowing comfortable application on the patient's skin.

To ensure a good infusion of these active principles subcutaneously, or in the bloodstream, at the appropriate dose, at the appropriate diffusion rate, and for the appropriate duration, the skilled person can easily set the following parameters:
- the ratio of the surface areas and the volumes of each compartment of the patch;
- the optional addition of one or more hydrophilic additive(s);
- the optional addition of one or more diffusion activator(s) or inhibitor(s);
- the optional addition of one or more solubilizer(s);
- the optional addition of one or more stabilizer(s);
- the optional addition of one or more absorption promoter(s), and;
- more generally, all types of additives well known to the skilled person allowing good control of the flow and stability of the tobacco leaf extract.

The skilled person will know which technique to use to set the parameters listed above based on the desired solubility and stability.

The various manufacturing parameters of the patch will be easily adapted by the skilled person to arrive at the desired dosage.

In a manner known per se, such a patch comprises a removable protective film which is intended to preserve the adhesive side to be applied to the skin after the patch has been manufactured and throughout its storage period. In a manner known per se, the skilled person will for example use polyester films, one side of which can be treated with anti-adherent silicones.

According to another embodiment, the composition according to the present invention is administered by means of a spraying or vaporization system containing the tobacco leaf extract as defined above. According to this embodiment, the pharmaceutical composition is provided in a form suitable for administration by spraying or vaporization. Advantageously, the pharmaceutical composition is provided in sprayer, vaporizer or aerosol form.

The sprayer, vaporizer or aerosol can be in the form of a sprayer, vaporizer or aerosol having a reservoir with one or more compartments. The practical execution of the sprayers, vaporizers or aerosols will be determined by the skilled person based on his general knowledge of the subject to obtain a controlled and prolonged systemic administration of the tobacco leaf extract.

The sprayer, vaporizer or aerosol will have one or more separate reservoir(s) containing the active principle(s) (including the tobacco leaf extract) in solution or suspension. The active principle(s) is/are then administered by spraying or vaporization on the area of the body to be treated. Spraying or vaporization can for example be carried out on the skin. The active principle(s) may be administered by spraying or vaporization into the mucous membranes.

To ensure a good infusion of these active principles subcutaneously, or in the bloodstream, at the appropriate dose, at the appropriate diffusion rate, and for the appropriate duration, the skilled person can easily set the following parameters:
- the ratio of the surface areas and the volumes of each compartment or reservoir of the sprayer, vaporizer or aerosol;
- the optional addition of one or more hydrophilic additive(s);
- the optional addition of one or more diffusion activator(s) or inhibitor(s);
- the optional addition of one or more solubilizer(s);
- the optional addition of one or more stabilizer(s);
- the optional addition of one or more absorption promoter(s), and;
- more generally, all types of additives well known to the skilled person allowing good control of the flow and stability of the tobacco leaf extract.

The skilled person will know which technique to use to set the parameters listed above based on the desired solubility and stability.

The different manufacturing parameters of the sprayer, vaporizer or aerosol will be easily adapted by the skilled person to arrive at the desired dosage.

According to a first embodiment, the pharmaceutical composition is provided in a form intended to be administered only once. According to this embodiment, the pharmaceutical composition is administered only once, thus allowing a reduction or a suppression of the positive reinforcements of tobacco and notably the urge to smoke.

According to another embodiment, the pharmaceutical composition is provided in a form intended to be administered several times, preferably two or three times. According to this embodiment, the pharmaceutical composition is preferably administered on days 0 and 10 or on days 0, 10 and 30, thus allowing a reduction or a suppression of the positive reinforcements of tobacco and notably the urge to smoke. In this embodiment, the dose injected the second time, and optionally the third time, is identical to the dose injected the first time.

According to a particular embodiment, the pharmaceutical composition according to the present invention may be administered with a composition comprising an active agent acting on negative reinforcement, such as a nicotine substitute, varenicline, bupropion or mixtures thereof. According to this embodiment, several specific modes of administration can be envisaged:

(i) administration, prior to the attempt to stop smoking, of the pharmaceutical composition according to the invention in order to reduce cigarette consumption, followed by administration of the active agent acting on negative reinforcement in order to limit the effects of the negative reinforcement, and in particular the sensation of withdrawal;

(ii) concomitant administration of the pharmaceutical composition according to the invention and of an active agent acting on negative reinforcement at the time of the attempt to stop smoking, with the aim of immediate cessation;

(iii) administration at the time of the attempt to stop smoking of an active agent acting on negative reinforcement, for example for 12 weeks after the attempt to stop, followed by administration of the pharmaceutical composition according to the invention, for example for 2 weeks after the end of the administration of the active agent acting on negative reinforcement, with the aim of preventing relapses.

Preparation of the Tobacco Leaf Extract

In a fourth aspect, the present invention concerns the preparation of a tobacco leaf extract according to the present invention.

Advantageously, the process for preparing the tobacco leaf extract according to the present invention comprises the following steps:

a. Curing of tobacco leaves,
b. Grinding of cured tobacco leaves to obtain ground cured tobacco leaves,
c. Extraction of the ground cured tobacco leaves under mechanical stirring with a solvent, for example an aqueous solvent, preferably an aqueous buffer solution with a pH between 6.0 and 8.5,
d. Separation of solid residues from the ground cured tobacco leaf extract solution by filtration or centrifugation to obtain a solid residue-free ground cured tobacco leaf extract solution,
e. Constant-volume filtration of the solution obtained in step d with a solvent, preferably an aqueous solvent, in an amount ranging from 2 to 12 times by volume, preferably 3 to 10 times by volume, preferably 4 to 8 times by volume, preferably 6 times by volume, based on the volume of the extract, and with a 10 kDa cut-off membrane,
f. Optionally lyophilization of the protein solution obtained in step e.

According to a particular embodiment, the curing of step a is carried out in open air, referred to as natural curing. In this case, curing is carried out in the presence of natural open air, outdoors or indoors. Curing can be carried out in an open or closed, covered or uncovered structure. Air-curing can for example be carried out in a natural curing barn. In this case, freshly harvested or pre-cured tobacco leaves are left to cure naturally under the effect of open air. The tobacco leaves can for example be hung in unheated ventilated barns. The tobacco leaves can for example be left to cure naturally until they turn brown. At this stage, there is practically no sugar left in the leaf. Advantageously, curing is carried out for a duration adapted to local climatic conditions, preferably for a minimum duration of one month. By way of example, curing can be carried out between September and December for harvests in central France. The tobacco leaves may be turned one or more times during curing, so as to allow uniform curing and to avoid the formation of condensation and the rotting or degradation of the leaves. The air-curing method can be used for example for Burley variety tobacco. According to a particular embodiment, the curing of step a is carried out in a natural curing barn.

According to another particular embodiment, the curing of step a is carried out in a heated curing barn. In this case, curing can be carried out in a barn or a structure heated to a suitable temperature.

According to another particular embodiment, the curing of step a is carried out by flue curing. In this case, curing can be carried out in a structure or a barn heated to a suitable temperature. Heat can be introduced into the structure or the barn through ducts connected to an external heat source. This controlled heating produces yellow-orange leaves. These leaves thus contain a high sugar content. Virginia tobacco can for example be cured using this method.

According to another particular embodiment, the curing of step a is carried out by sun curing. In this case, the tobacco leaves can be spread on racks and exposed to the sun for 12 to 30 days. Under direct light and heat from the sun, the leaves turn yellow or orange and retain a high sugar content. Oriental tobacco is generally cured using this method.

According to another particular embodiment, the curing of step a is carried out by fire curing. In this case, small pieces of wood can be burned beneath the tobacco leaves, which cure while absorbing a "smoky" aroma.

Advantageously, the curing of step a promotes the degradation of high molecular mass tobacco proteins, such as RuBisCO, for example by hydrolysis mechanisms.

Steps c to e correspond to the extraction, filtration and diafiltration steps of the type described in U.S. Pat. No. 5,770,698 (column 6, line 47 to column 7, line 7) and patent application US 2009/0162403 (paragraphs [0032] to [0040]).

Preferably, the extraction in step c is carried out at a temperature between 4 and 20° C., preferably between 4 and 10° C.

Preferably, the extraction in step c is carried out for 12 to 36 h, preferably 22 to 26 h, preferably 24 h.

According to a particular embodiment, the solvent used in step c is an aqueous solvent. Preferably, the aqueous solvent used in step c is an aqueous buffer solution of ammonium bicarbonate, preferably at a concentration between 2 and 6 g/L, preferably 4 g/L.

Of course, other types of solvents can be used to carry out the extraction of step c. The extraction of step c can be carried out with an organic or inorganic solvent, or with a mixture of organic and/or inorganic solvents.

To ensure good extraction efficiency and yield, and to obtain an extract of good quality with the desired purity properties and composition, the skilled person will easily know how to select the appropriate solvent(s) according to the following criteria:

- the polarity of the solvent or solvent mixture (polar or non-polar);
- the physical state of the solvent or solvent mixture (for example liquid, solid, supercritical or gaseous);
- the chemical nature of the solvent or solvent mixture (for example organic or inorganic);
- the charge of the solvent or solvent mixture (for example ionic or non-ionic);
- the origin of the solvent or solvent mixture;
- the miscibility of the solvent or solvent mixture;
- the solubility of the solvent or solvent mixture.

The skilled person will know which technique to use to select the solvent(s) corresponding to these criteria, based on the desired extraction yield and extract purity and composition.

Preferably, the extraction in step c is carried out by suspending the ground cured tobacco leaves in a buffer solution, preferably at a concentration of ground cured tobacco leaves in the buffer solution of 30 to 70 g/L, preferably 40 to 60 g/L, and more preferentially 50 g/L. The suspended solid residues are then removed by filtration, for example by Büchner filtration (step d), in order to obtain ground cured tobacco leaves free of solid residue. Preferably, the aqueous solvent used in step d is water for injection (WFI).

Advantageously, step e removes more than 99% of molecules of molecular mass less than 10 kDa and notably free amino acids, proteins and peptides of molecular mass less than 10 kDa and protein residues of molecular mass less than 10 kDa resulting from the degradation of the proteins of step a.

Preferably, the protein solution obtained in step e is subjected to a step e' of sterilizing filtration, prior to step f.

The tobacco leaf extract according to the invention obtained at the end of the process described above may be stored as obtained at the end of step d' of sterilizing filtration, or lyophilized as obtained at the end of step f.

Preparation of the Pharmaceutical Composition Comprising the Tobacco Leaf Extract In a fifth aspect, the present invention concerns the preparation of the pharmaceutical composition comprising the tobacco leaf extract according to the invention.

The pharmaceutical composition may be prepared by a process comprising the following steps:
  a. Preparation of a tobacco leaf extract as defined above,
  b. Adjustment of the protein concentration so as to obtain a protein concentration ranging from 100 to 200 µg/mL,
  c. Addition of the pharmaceutically acceptable excipient(s), and
  d. Optionally, addition of adjuvant(s) to this extract, preferably addition of mannitol.

The tobacco leaf extract used in step b can be either that obtained directly after the step of diafiltration on a 10 kDa cut-off membrane, or that obtained after the step of sterilizing diafiltration, or the tobacco leaf extract which is lyophilized then reconstituted for example in saline solution or water.

Advantageously, the concentration in step b can be adjusted:
  either by dilution with water in order to lower the protein concentration,
  or by diafiltration in order to increase the protein concentration.

A pharmaceutically acceptable excipient particularly preferred in step c is water.

The adjuvants that can be added in step d may be notably swelling agents such as for example a sugar such as lactose, sucrose, trehalose, sorbitol, glucose, raffinose, mannitol, preferably lactose, sucrose, trehalose, glucose, or mannitol, an amino acid such as arginine, glycine or histidine, preferably glycine, or polymers of the dextran or polyethylene glycol type; or mixtures thereof.

According to a particular embodiment, step d comprises at least the addition of mannitol.

Kit Comprising the Pharmaceutical Composition Comprising the Tobacco Leaf Extract In a sixth aspect, the present invention concerns a kit comprising doses of the tobacco leaf extract or of the pharmaceutical composition according to the invention.

According to a first embodiment, the kit comprises one or more dose(s) of tobacco leaf extract, preferably in lyophilized form, as well as one or more dose(s) of saline solution or of WFI to prepare the pharmaceutical composition according to the invention just before administration.

According to another embodiment, the kit comprises one or more dose(s) of pharmaceutical composition ready to be administered to the patient.

The kit may optionally comprise one or more syringe(s) in order to administer the pharmaceutical composition by subcutaneous injection.

The kit may optionally comprise one or more patch(s) in order to administer the pharmaceutical composition transdermally.

The following examples aim to illustrate the present invention.

EXAMPLES

Example 1: Preparation of a Tobacco Leaf Extract According to the Invention

Burley tobacco leaves are used to prepare the extract.

100 g of Burley tobacco leaves cured naturally for about three months (in central France, between September and December) are ground. The ground leaves are suspended for 24 h at a temperature of 4 to 10° C. in 1 892 g of WFI to which 8 g of ammonium bicarbonate has been added. The suspended solid residues are then removed by Büchner filtration.

A 0.2 µm clarifying filtration of the extract is then carried out. The extract obtained is brown in colour. The extract is then weighed to determine the volume of WFI to be used in the constant-volume diafiltration step; in this case the mass of the liquid extract is 1 680 g.

An extraction of the proteins of this solid residue-free ground cured tobacco leaf extract is then performed: 10 080 g of WFI is then added to the solid residue-free ground cured tobacco leaf extract. The 11 760 g of solution thus obtained is diafiltered at constant volume against 6 times the volume with a 10 kDa cut-off (MerckMillipore) until the mass of the retentate is reduced to 1 680 g.

The retentate obtained after diafiltration is a protein mixture in which proteins of molecular mass less than 10 kDa are detected with a concentration 99% lower than their initial concentration. The colour of the retentate obtained is between B2 and B3 according to the measurement scale defined in EUROPEAN PHARMACOPOEIA 5.0, 2.2.2, Degree of coloration of liquids.

This diafiltrate can be lyophilized, after addition of mannitol for example, using an SMH 150 lyophilizer, to obtain a lyophilized tobacco leaf extract.

Example 2: Determination of the Protein Composition of the Tobacco Leaf Extract Prepared According to Example 1

The proteins of the tobacco leaf extract of example 1 are first separated on a polyacrylamide gel. To this end, the extract to be analysed is added to a NuPage® Bis-Tris gel (4-12%) and electrophoresis is performed at 200 V for 35 min, before being brought into contact with 20 mL of Instant Blue for 1 h then rinsed with water overnight. The selected polyacrylamide gel bands are cut out (6 bands) and then destained with 50 mM $NH_4CO_3$/$CH_3CN$ (50/50) buffer. The disulphide bridges are then reduced with 10 mM dithiothreitol/50 mM $NH_4CO_3$ solution for 40 min at 55° C. The reduced cysteines are then alkylated with 100 mM iodoacetamide/50 mM $NH_4CO_3$ solution for 30 min at room temperature and in the dark.

The protein solution thus obtained is digested with an enzyme to obtain protein or peptide fragments: the digestion is carried out with trypsin (trypsin V5111, Promega) in an amount adapted to the staining of the polyacrylamide gel bands in 50 mM $NH_4CO_3$ solution overnight at 37° C.

The peptides of the peptide digestate are then separated by liquid nanochromatography (U3000 NanoLC System, ThermoFischer Scientific) with preconcentration on PepMap C18 micro-precolumn (5 µm; 100 Å; 300 µm×5 mm; ThermoFisher Scientific) then elution on PepMap C18 nanocolumn (3 µm; 100 Å; 75 µm×250 mm; ThermoFisher Scientific) in linear gradient mode; buffer A 0.1% HCOOH in $H_2O$/$CH_3CN$ (95/5), buffer B 0.1% HCOOH in $H_2O$/$CH_3CN$ (20/80), Gradient 0 to 60% B in 60 min, flow rate 300 µL/min).

The peptides are then analysed by mass spectrometry on an LTQ Velos instrument (Dual Pressure Linear Ion Trap; ThermoFisher Scientific) equipped with a nanospray source (ThermoFisher Scientific) and coupled to the U3000 NanoLC device. Data are acquired with the Excalibur 2.1 software (ThermoFisher Scientific) in positive mode by cycle of an MS scan from m/z 400 to 1600 in "Resolution Enhanced" mode followed by MSMS scans in "Normal Resolution" mode on the 20 most intense MS ions (charge 2 and higher) in CID mode under helium with collision energy of 35 eV. Previously fragmented MS ions are dynamically excluded for 30 s with a mass tolerance of 50 mmu.

The masses of the peptides and their fragments are compared with existing data in the databases for purposes of identification. To this end, the MS and MSMS data are processed with the ProteomeDiscoverer 1.4 software according to the MASCOT search algorithm (Version 2.4) and the UniprotKB/Swiss-Prot database (April 2015 release) reduced to the TOBAC species is queried.

The identification of the proteins is validated according to the confidence value p of less than 0.05. Only proteins identified with at least 2 peptides of maximum confidence are retained.

The scores of each protein thus identified allow only a relative classification of proteins between them, this classification being correlated to the concentrations of these proteins. The absolute values of these scores depend on the operating conditions, the test sample and the amounts deposited.

The list of the 12 proteins thus identified and classified in descending order of their scores (from the most present to the least present) is as follows:
- P36401; E13H_TOBAC; Glucan endo-1,3-beta-glucosidase, acidic isoform PR-Q' (EC 3.2.1.39) ((1→3)-beta-glucan endohydrolase) ((1→3)-beta-glucanase) (Beta-1,3-endoglucanase) (PR-35); MM: 36995 Da
- P17513; CHIP_TOBAC; Acidic endochitinase P (EC 3.2.1.14) (Pathogenesis-related protein P) (PR-P); MM: 27469 Da
- P17514; CHIQ_TOBAC; Acidic endochitinase Q (EC 3.2.1.14) (Pathogenesis-related protein Q) (PR-Q); MM: 27633 Da
- P27666; E13F_TOBAC; Glucan endo-1,3-beta-glucosidase, basic vacuolar isoform GLB (EC 3.2.1.39) ((1→3)-beta-glucan endohydrolase) ((1→3)-beta-glucanase) (Beta-1,3-endoglucanase, basic) (Glucanase GLB); MM: 40443 Da
- P14170; OSMO_TOBAC; Osmotin; MM: 26681 Da
- P24091; CHI2_TOBAC; Endochitinase B (CHN-B) (EC 3.2.1.14); MM: 34721 Da
- P11965; PERX_TOBAC; Lignin-forming anionic peroxidase (EC 1.11.1.7) (TOPA); MM: 34674 Da P13046; PRR1_TOBAC; Pathogenesis-related protein R major form (Thaumatin-like protein E22); MM: 24667 Da P29062; PR4A_TOBAC; Pathogenesis-related protein PR-4A; MM: 16221 Da Q03199; IPIB_TOBAC; Proteinase inhibitor I-B (PI-IB) (Inhibitor of microbial serine proteinases major isoform); MM: 11916 Da Q03198; IPIA_TOBAC; Proteinase inhibitor I-A (PI-IA) (Inhibitor of microbial serine proteinases minor isoform); MM: 11880 Da P29063; PR4B_TOBAC; Pathogenesis-related protein PR-4B; MM: 16235 Da The tobacco leaf extract preparation process thus makes it possible to concentrate certain proteins and to remove others. Thus, of the 759 Nicotiana tabacum proteins listed in Swiss-Prot, only 6 families and 12 proteins are predominantly present in the tobacco leaf extract prepared according to example 1. The 12 proteins that are predominantly present in the tobacco leaf extract prepared according to example 1 have a molecular mass between 10 and 50 kDa.

Example 3: Determination of Protein Content

The protein content in the tobacco leaf extract according to example 1 (before and after the diafiltration step) was determined according to the Bradford method.

The extract of example 1 is dissolved in saline solution.

Three standard protein solutions were prepared: 50 µL of a 2 mg/mL bovine serum albumin solution (Sigma Aldrich, product number P0834) is diluted 20 times with 950 µL of saline solution in order to obtain standardized solutions at exactly 100 µg/mL.

Each tube tested contains 80 µl of protein sample and 920 µL of Bradford reagent (Sigma Aldrich product number B6916). After the Bradford reagent is added to each tube, the tubes are gently shaken to create a vortex, then incubated for 5 min at room temperature. The samples are transferred to 1.5 mL cuvettes and their absorbance is measured at 595 nm for 1 h.

The protein concentration was determined by comparison with the standard protein solutions prepared.

The measured protein amounts are:
before diafiltration: 295.45+/−9.91 µg/mL
after diafiltration: 160.61+/−1.31 µg/mL.

The electrophoretic profile of the tobacco leaf extract according to example 1 was determined after the diafiltration step. Amounts of 2, 5, 10 and 15 µg of proteins were deposited on a NuPage gel.

The 4%-12% Nupage gel was prepared for 35 minutes then placed in 20 ml of Coomassie Blue for 1 h and rinsed with water overnight. The gel was analysed using Biorad's ChemiDoc™ XRS system with the Image Lab™ software.

Three main bands are detected around 15 kDa and 30 kDa (FIG. 1). Two other bands are also perceptible at about 40 kDa.

The results show that the amount of proteins of molecular mass greater than 100 kDa detected is small compared with the amount of proteins of molecular mass between 10 and 50 kDa, in this tobacco leaf extract.

Example 4: Influence of Diafiltration Volume on the Removal of Molecules of Molecular Mass Less than 10 kDa in a Tobacco Leaf Extract According to the Invention The removal of molecules of molecular weight less than 10 kDa in the tobacco leaf extract according to example 1 was monitored during the diafiltration step according to the diafiltration volume used. Monitoring is performed by gas chromatography assay of an analytical tracer (nicotine) of molecular mass less than 10 kDa.

The results are presented in the following table:

| Samples according to diafiltration volume | Peak area of the analytical tracer | Percentage of the analytical tracer remaining |
| --- | --- | --- |
| Before diafiltration | 54913 | 100 % |
| Diafiltration × 3 volume | 2630 | 4.79 % |
| Diafiltration × 4 volume | 809 | 1.47% |
| Diafiltration × 5 volume | 247 | 0.045 % |
| Diafiltration × 6 volume | NQ | NQ |

The removal of molecules of molecular weight less than 10 kDa is increasingly effective when the diafiltration volume increases and is total when this diafiltration volume is 6 times the initial volume.

Example 5: Biological Activity of the Extract of Example 1 In Vitro on Human Mononuclear Cells and In Vivo on Mice Materials and Methods:

Products Used

PMA/Ionomycin (Sigma-Aldrich product number P8139/10634)

BSA (Sigma Aldrich product number A7020)

PBS (PAA Laboratories product number H15-002)

Tween 20 (Sigma Aldrich product number P1379)

Goat anti-mouse IgG (g chain specific)—Alkaline Phosphatase (Southern Biotech product number 1030-04)

Biotin-anti mouse IgE (Biolegend product number BLE406904)

Streptavidin—Alkaline Phosphatase (Southern Biotech product number 7100-04)

Cell Preparation and Stimulation Mode

Peripheral blood mononuclear cells from different healthy donors were isolated by centrifugation on a density gradient (separation medium: LMS 1077 PAA Laboratories). The mononuclear cells obtained were stimulated with the extract according to example 1 at different dilutions for 24 h or 48 h. The supernatants were removed and stored at −80° C. after 24 h or 48 h of stimulation for cytokine profile analysis using the Luminex technique. After 24 h of stimulation the cells were also taken for phenotypic analysis by flow cytometry.

Cytometric Phenotypic Analysis

The cells were first stained with a viability marker (Dye eFluor 450 (65-0863-14 eBioscience) and then with antibodies directly coupled to fluorochromes for the detection of different membrane markers. T and B lymphocyte populations were identified with markers CD3 and CD19. NK cells were detected either with marker NKp46 or the combination of markers CD56 and CD16 or via CD56 expression in the absence of CD3. From these cell populations, "gates" were set to analyse different activation markers (CD69, CD25, HLA-DR).

The list of antibodies used for the phenotypic cytometric analysis is given in the following table:

|  | Clone | Product number and supplier |
|---|---|---|
| Anti-CD45-Krome Orange | J.33 | A96416; Beckman Coulter |
| Anti-CD56 APC | B159 | 555518; Becton Dickinson |
| Anti-CD25PC7 | M-A251 | 557741; Becton Dickinson |
| Anti-CD25 PC5 | B1.49.9 | IM2646; Beckman Coulter |
| Anti-CD69 FITC | FN50 | 557049; Becton Dickinson |
| Anti-CD69 PE | L78 | 341652; Becton Dickinson |
| Anti-CD3 ECD | UCHT1 | A07748; Beckman Coulter |
| Anti-KpP46 APC | 9E2/NKp46 | 558051; Becton Dickinson |
| Anti-CD19 FITC | HIB19 | 11-0199-42; eBioscience |
| Anti-HLA-DR PE | G46-6 | 347401; Becton Dickinson |

Isotype controls were used in each experiment and a compensation matrix was created for this multiparametric phenotypic analysis.

The stained samples were analysed on a Navios cytometer (Beckman Coulter 10-colour) with a minimum acquisition of 100 000 events per tube. The acquired data were then analysed on the Kaluza software.

Analysis of the Cytokine Secretion Profile by Luminex and ELISA

This technology, based on ELISA and cytometry principles, allows several analytes to be assayed simultaneously.

Unique colour-coded microbeads are coupled to capture antibodies specific for each analyte. After incubation with the samples to be assayed, detection antibodies coupled to a fluorochrome will allow analysis by a dual-laser optical system (Bio-plex 200 system Bio-rad). The first laser identifies the microbead and the second quantifies the detection antibodies coupled to the fluorochrome. 17 analytes can be assayed with the Bio-Plex Pro Human Cytokine Grp1 panel 17 plex kit (Bio-rad) on samples taken during the various stimulation experiments performed on the cells. The cells stimulated by the culture medium without the tobacco leaf extract according to example 1 make it possible to obtain the basal level for each cytokine.

IL-8 ELISA is based on a conventional immunoenzymatic sandwich technique. The commercial kits used were purchased from Eurobio-Diaclone (Besancon).

Immunization of Mice with the Tobacco Leaf Extract According to Example 1

Seven-week-old female C57BL/6 and Balb/c mice were purchased from Charles River (L'Arbresles, France). The mice were immunized on days 0 and 21 intraperitoneally with 200 µL of the tobacco leaf extract according to example 1 lyophilized and reconstituted in 5 mL of saline solution. Blood was collected from all mice before and after immunization. After centrifugation, the serum was frozen at −20° C.

IgG and IgE ELISA

For the ELISA experiment, one vial of the product was reconstituted with 2.5 mL of carbonate-bicarbonate buffer (0.1M, pH 9). Nunc Maxisorb 96W plates were incubated with 100 µL of the tobacco leaf extract lyophilized according to example 1 then reconstituted and incubated for 18 h. After washing the plates with PBS-0.05% Tween buffer, the plates are saturated with 200 µL of PBS-1% BSA buffer for one hour at room temperature. After washing the plates with PBS-0.05% Tween buffer, 100 µL of mouse serum, diluted to 1/20 in PBS-1% BSA, is incubated for 2 hours at room temperature.

Elisa IgG:

After washing with PBS-Tween 20 buffer, 100 µL of a goat anti-mouse IgG secondary antibody coupled to alkaline phosphatase (Southern Biotechnology product number 1030-04) and diluted in PBS-1% BSA is incubated for 1 hour at temperature. After washes with PBS-0.05% Tween, 100 µL of p-Nitrophenyl phosphate substrate (Sigma pNPP) of alkaline phosphatase is added and left 15 min at room temperature in the dark. The reaction is then stopped by adding 50 µL of 3M NaOH and the optical densities (OD) are read at 405 nm.

Elisa IgE

After washing with PBS-Tween 20 buffer, 100 µL of a rat anti-mouse IgE secondary antibody coupled to biotin (Biolegend product number BLE406904) and diluted in PBS-1% BSA is incubated for 1 hour at room temperature. After washes with PBS-0.05% Tween, 100 µL of streptavidin coupled to alkaline phosphatase (Southern Biotechnology product number 7100-04) is added and incubated for 1 hour at room temperature (dilution 112000th in PBS-1% BSA according to the supplier's recommendations). After further washes with PBS-0.05% Tween, 100 µL of pNPP substrate of alkaline phosphatase is added and left 15 min at room temperature in the dark. The reaction is then stopped by adding 50 µL of 3M NaOH and the optical densities (OD) are read at 405 nm.

Results:

The Tobacco Leaf Extract According to Example 1 Causes a Specific IgG Humoral Response in Mice.

Figure 2:
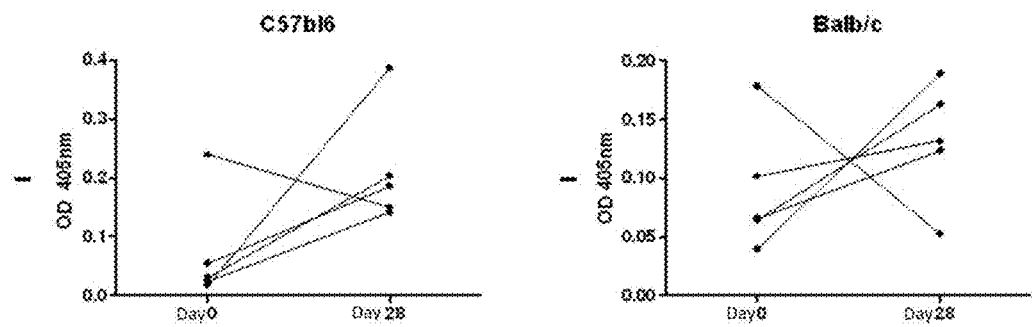
FIG. 2. IgG induction after injection of the tobacco leaf extract according to example 1 in mice.
Figure 3A:
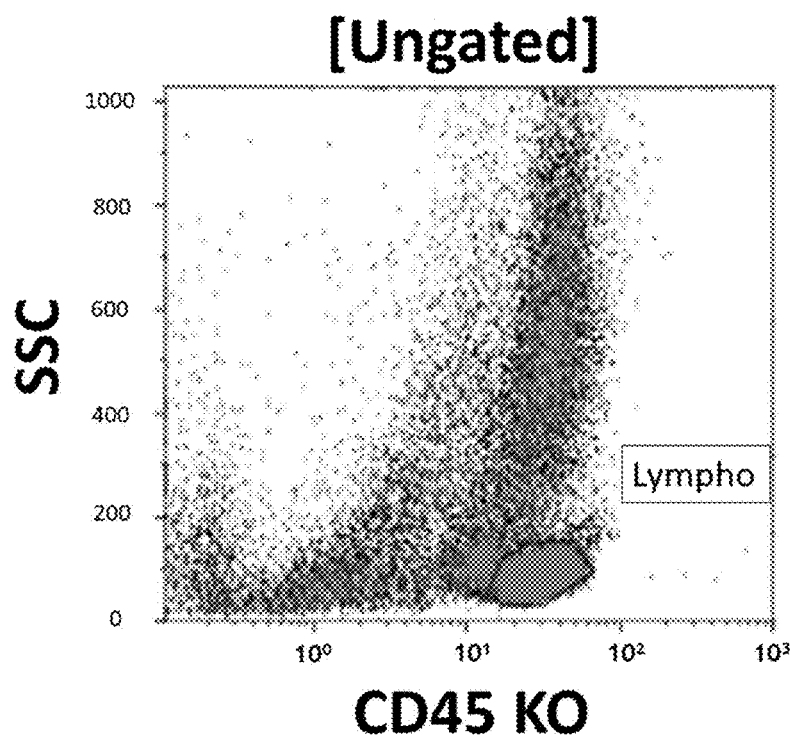
FIGS. 3A-3I. Illustration of immunophenotyping for the characterization of activated immune cells.
Figure 3B:
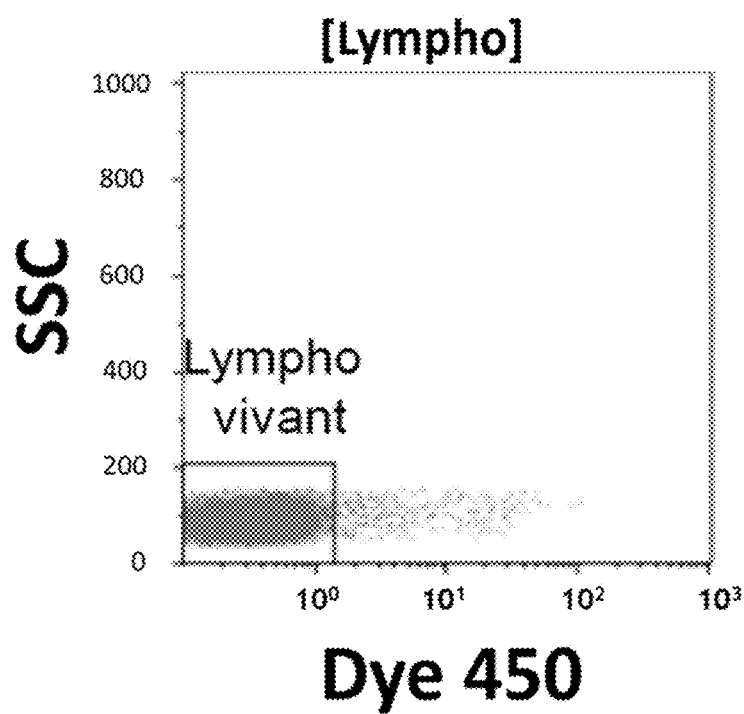
Figure 3C:
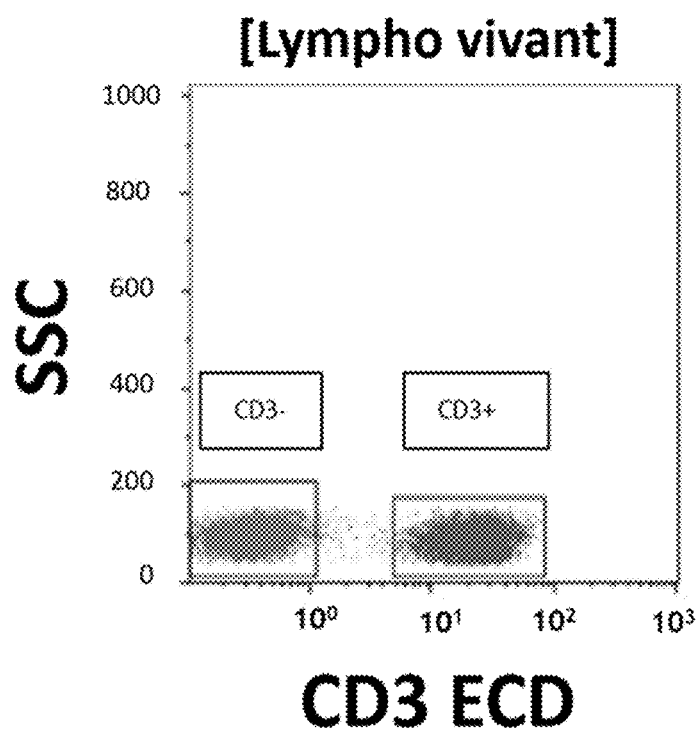
Figure 3D:
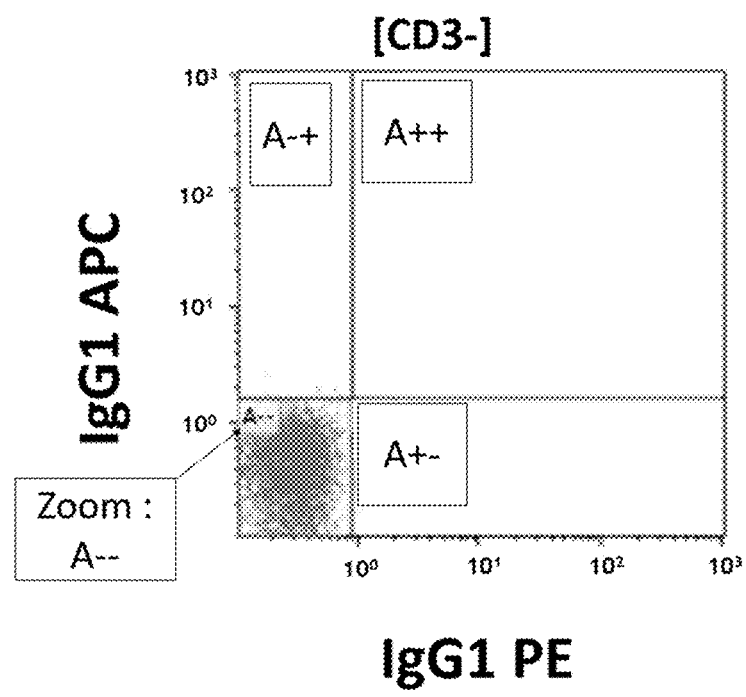
Figure 3E:
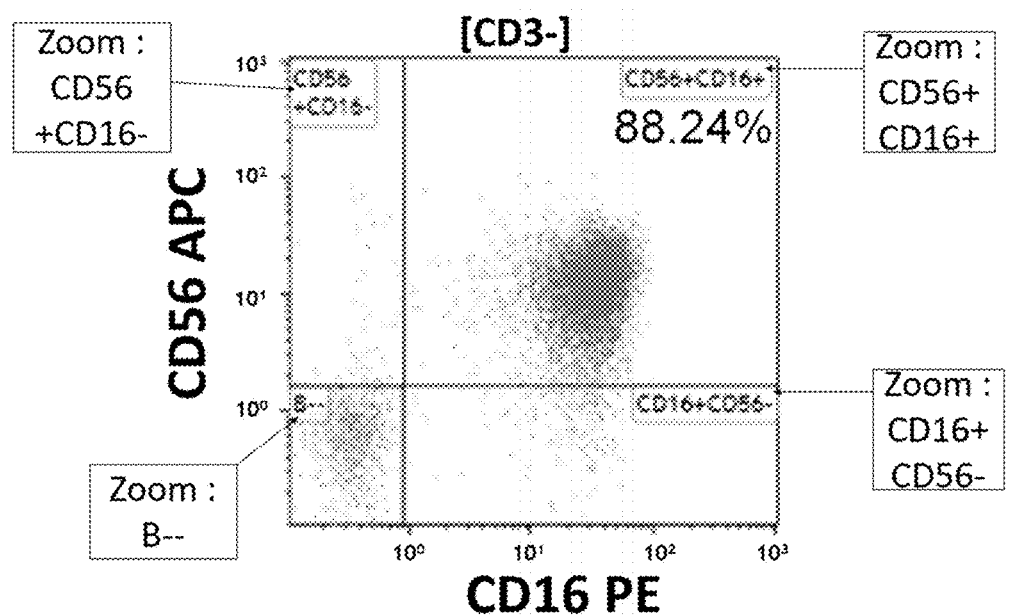
Figure 3F:
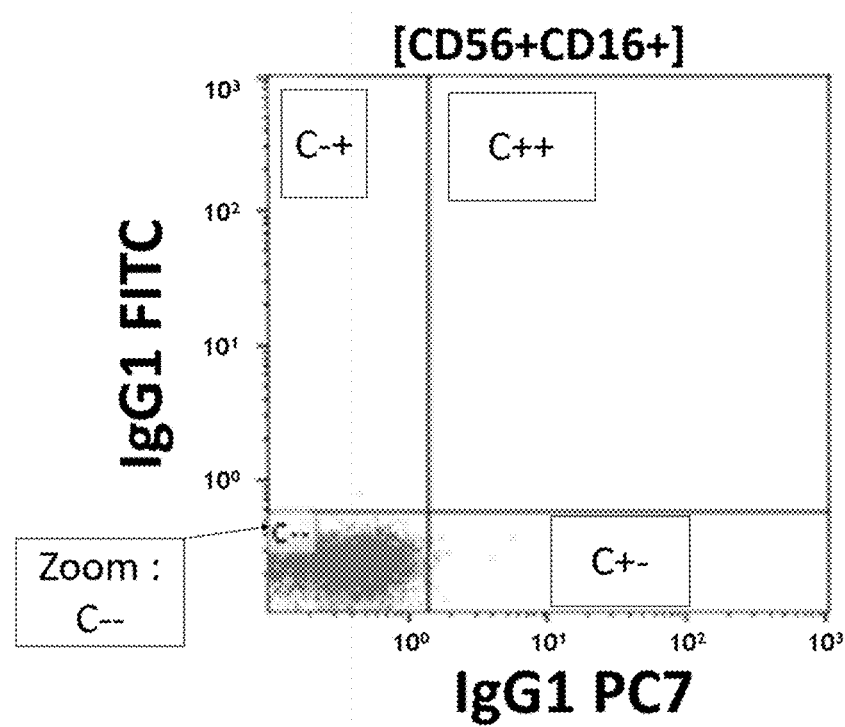
Figure 3G:
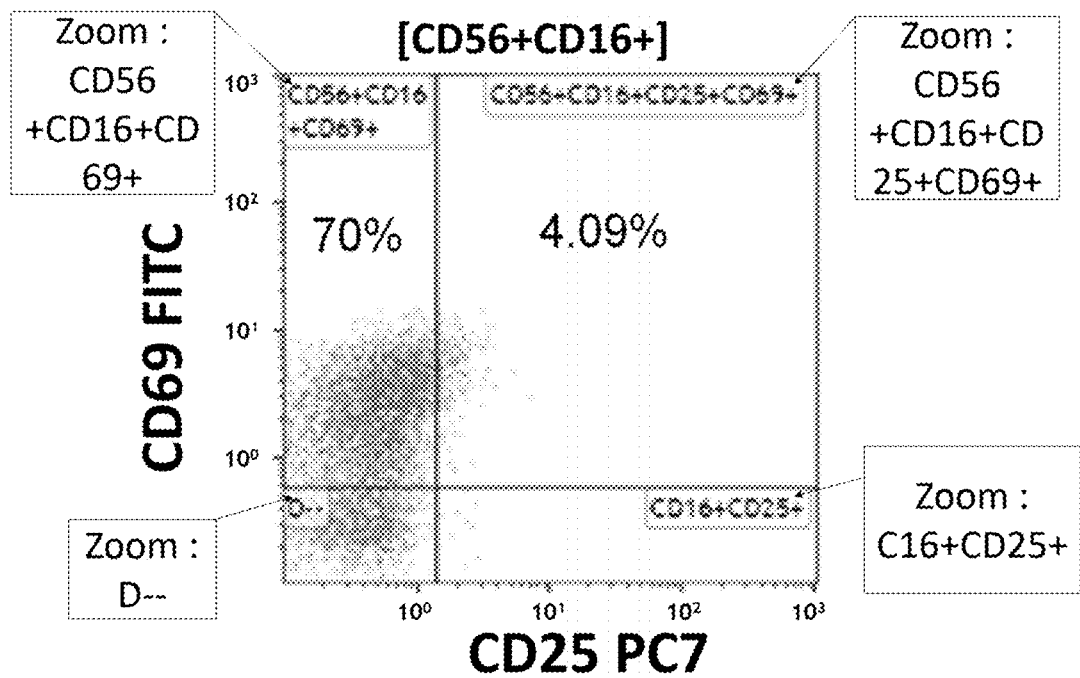
Figure 3H:
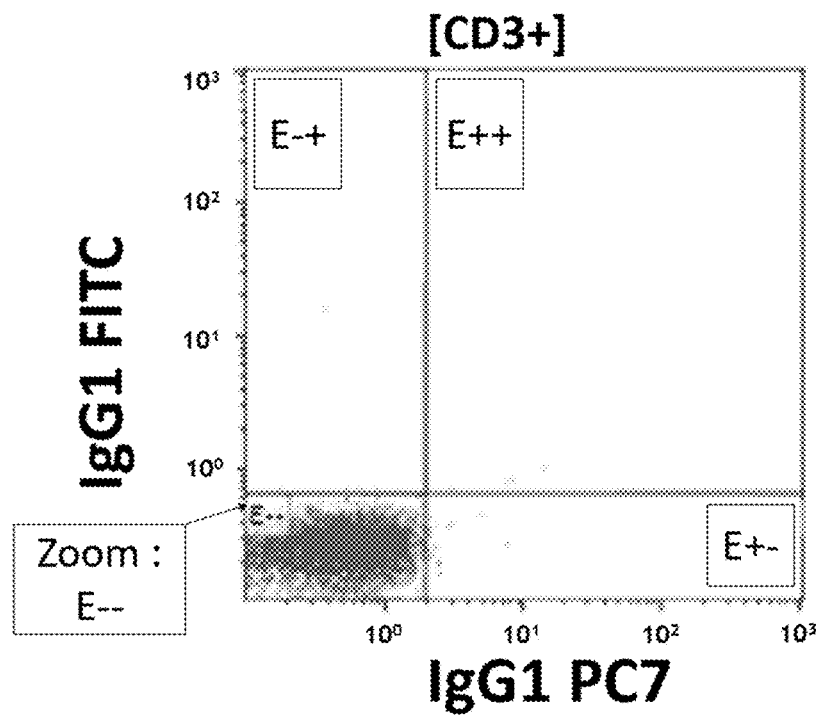
Figure 3I:
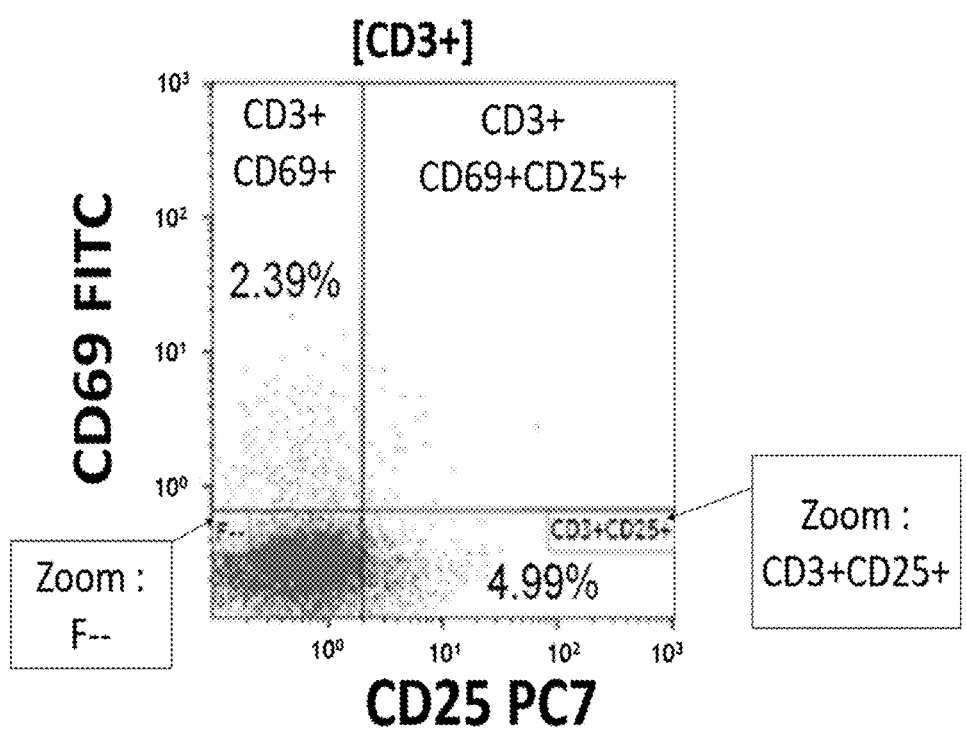

After 2 immunizations of the mice with the tobacco leaf extract lyophilized according to example 1 and reconstituted in 5 mL of saline solution, IgG induction was observed against components of the product. Thus, 4/5 C57BL/6 mice and 4/5 Balb/c mice showed an increase in their IgG against the tobacco leaf extract on day 28, i.e. 7 days after the 2nd vaccination (FIG. 2). The only mouse in each group which did not respond had basal IgG antibody levels. Antibody titres appear lower in the Balb/c mice than in the C57BL/6 mice (FIG. 2).

However, no IgE humoral response after 2 vaccinations of the mice with the tobacco leaf extract was detected. Optical densities (OD) were less than 0.05 in all assays performed on the different sera.

Figure 4:
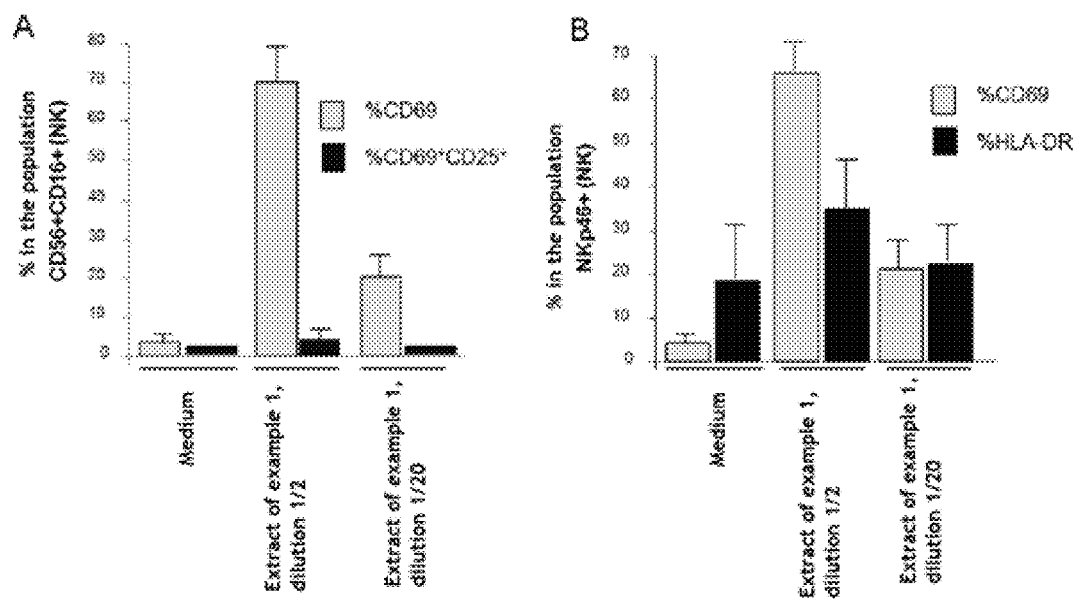
FIG. 4. Activation of natural killer cells by the tobacco leaf extract according to example 1.

The Tobacco Leaf Extract Preferentially Activates Peripheral Blood Natural Killer Cells After isolation of mononuclear cells from peripheral blood by density gradient (Ficoll), different cell populations (T and B lymphocytes, NK cells, etc.) can be characterized (FIG. 3A-3I). Thus, NK cells were identified by markers CD56 and CD16 in the CD3 negative population or by marker NKp46. After incubation of the mononuclear cells with the tobacco leaf extract according to example 1, an increase in expression of activation markers CD69, CD25 and HLA-DR was observed on the NK cells, identified both by markers CD16+CD56+(CD3−) (FIG. 4A) and by marker NKp46 (FIG. 4B). The results are more distinct with the tobacco leaf extract diluted to 1/2 and for CD69 expression. Thus, more than 60% of NK cells express marker CD69 24 hours after contact with the tobacco leaf extract (FIG. 4A-B). At rest, less than 5% of blood NK cells express CD69.

Figure 5:
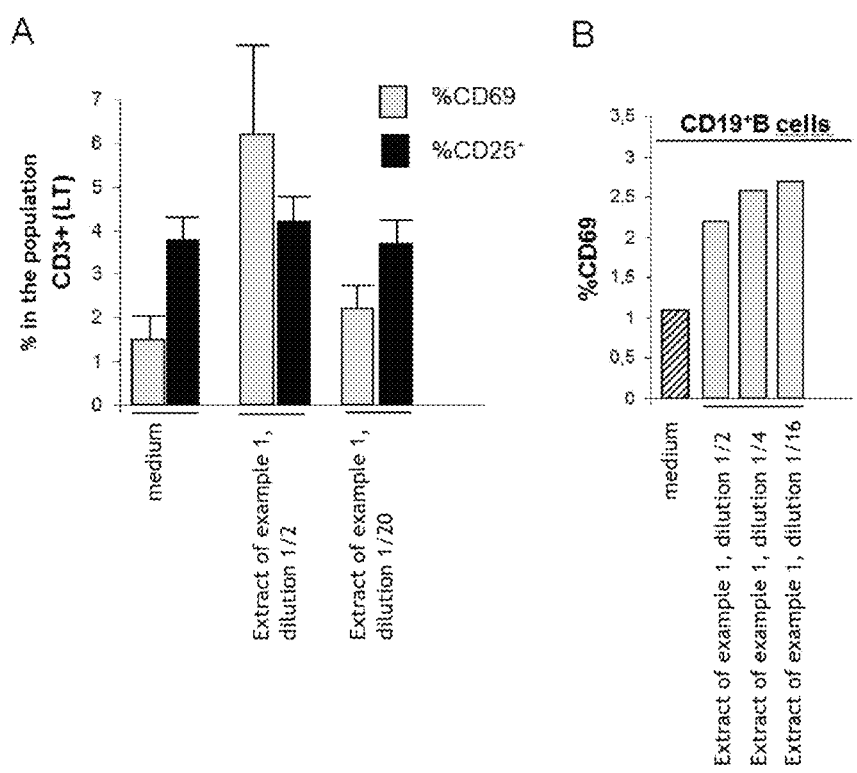
FIG. 5. Activity of the tobacco leaf extract according to example 1 on T and B lymphocytes.

The effect of the tobacco leaf extract on activation of peripheral blood lymphocytes is much weaker. Thus, at rest 2% of T lymphocytes express CD69 and this expression increases to 6% after 24 hours of culture with the tobacco leaf extract (FIG. 5A). CD25 expression is not increased on T lymphocytes sensitized with the tobacco leaf extract (FIG. 5A). Similarly, on peripheral blood B lymphocytes, the tobacco leaf extract has no significant activity, as less than 3% of B lymphocytes express CD69 after 24 hours of co-culture with this extract (FIG. 5B).

Profile of Cytokines Induced by the Tobacco Leaf Extract According to Example 1 on Human Blood Mononuclear Cells Peripheral blood mononuclear cells were brought into contact for 24 hours with the tobacco leaf extract lyophilized according to example 1 and reconstituted with 5 mL of PBS at different dilutions (1/2 or 1/20) and assays of cytokines, chemokines and growth factors were performed by Luminex in the supernatant.

Figure 6:
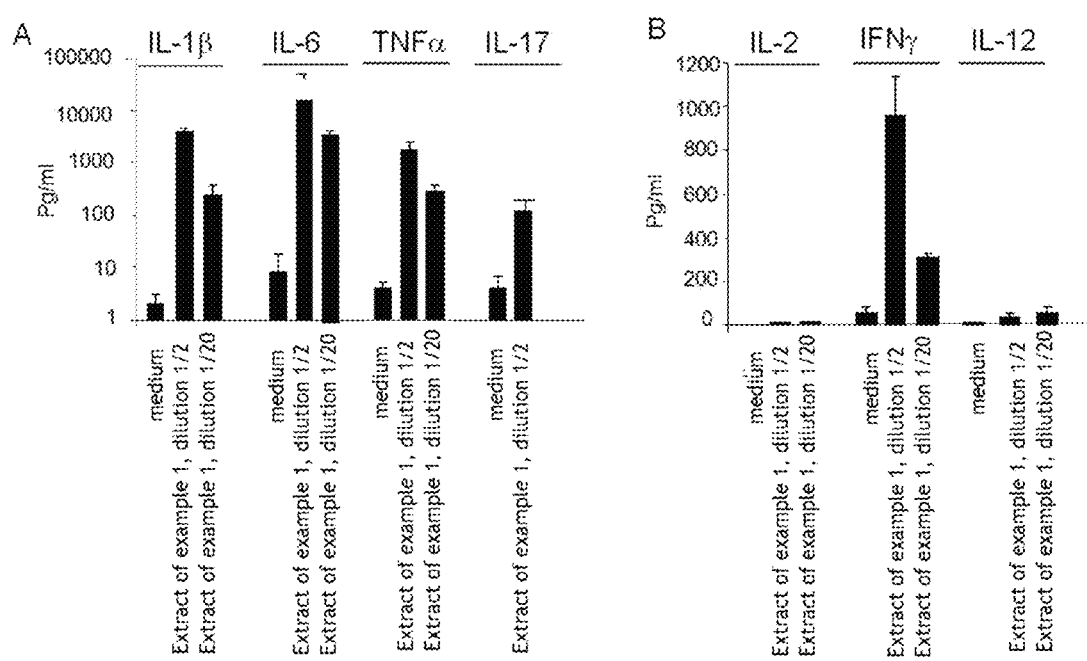
FIG. 6. Induction of pro-inflammatory cytokines and of IFNγ by the tobacco leaf extract according to example 1.

FIG. 6 shows a strong induction of pro-inflammatory cytokines (IL-1ß, IL-6, TNFα, IL-17) by the tobacco leaf extract. For example, the basal levels of these cytokines when the mononuclear cells are not placed in the presence of the tobacco leaf extract are less than 10 pg/mL (FIG. 6A).

Figure 7:
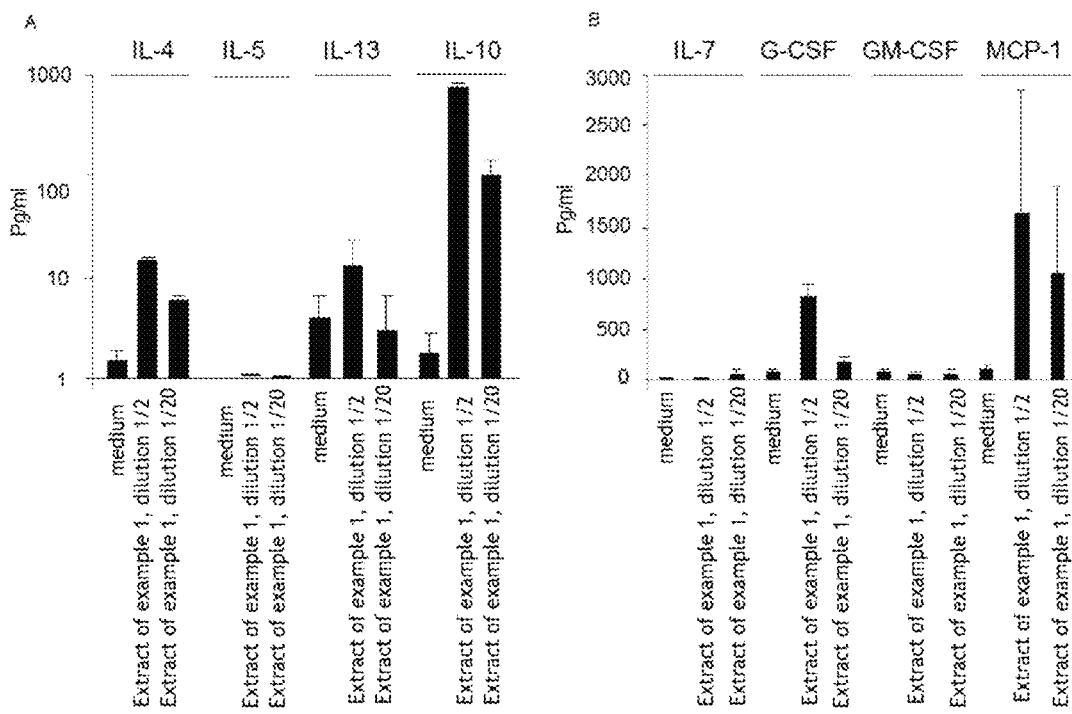
FIG. 7. Induction of TH2 cytokines and of chemokines and hematopoietic growth factor by the tobacco leaf extract according to example 1.

Concentrations of cytokines IL-1ß, IL-6 and TNFα are measured at over 1 000 pg/mL after incubation with the tobacco leaf extract diluted to ½ (FIG. 6A). This clear induction of pro-inflammatory cytokines is also observed when the tobacco leaf extract is diluted to 1/20 (FIG. 6A). The results are fairly homogeneous between the different donors tested. Among the TH1 cytokines (IL-2, IFNγ, IL-12) promoting cell-mediated immunity, only IFNγ is significantly stimulated by the tobacco leaf extract diluted to 1/2 and to 1/20 (FIG. 6B). The tobacco leaf extract induces very low concentrations of TH2 cytokines (IL-4, IL-5, IL-13) of the order of a few pg/mL (FIG. 7A). In contrast, the tobacco leaf extract stimulates IL-10 production by mononuclear cells with levels of 750 µg/mL found in the supernatant of cells brought into contact with the tobacco leaf extract diluted to 1/2 (FIG. 7A). IL-10 was originally considered a TH2 cytokine but it can also be produced by regulatory T lymphocytes called Tr1.

We have shown that the tobacco leaf extract can also induce the production of hematopoietic growth factors such as G-CSF which promotes the expansion and recruitment of neutrophils and chemokines such as MCP-1 known to exert a chemotactic effect on macrophages (FIG. 7B). However, the tobacco leaf extract does not appear to significantly stimulate other growth factors such as IL-7 or GM-CSF (FIG. 7B). The same cytokine/chemokine profile was found when the assays were performed on supernatants collected 48 hours after culture with the tobacco leaf extract.

Conclusion

The tobacco leaf extract according to example 1 is capable of inducing a specific IgG humoral response directed against proteins present in the product in two mouse lines of different genetic background.

No IgE humoral response was observed after two administrations of the substance in these same mice.

In vitro, the tobacco leaf extract according to example 1 preferentially induces the activation of NK cells among peripheral blood mononuclear cells. This activation is reflected by the increased expression of CD69, CD25 and HLA-DR molecules.

The tobacco leaf extract according to example 1 induces in vitro pro-inflammatory cytokines such as IL-1ß, IL6, IL-17, IL-8 and TNFα. These cytokines are present in high concentrations in the culture supernatant collected 24 hours after stimulation.

The tobacco leaf extract according to example 1 also induces IFNγ, IL-10, G-CSF and MCP-1. However, this extract does not significantly induce the production of TH2 cytokines (IL-4, IL-5, IL-13).

Example 6: Toxicological Study of a Tobacco Leaf Extract According to Example 1

Materials and Methods:

All studies below were performed with the tobacco leaf extract according to example 1. The route of administration is subcutaneous in all cases. The toxicology studies were conducted on rodents (Han Wistar rats). The toxicological studies were carried out according to the OECD principles of good laboratory practice (Mutual Acceptance of Data (MAD) in the assessment of data, 26 Nov. 1997 (C(97) 186 Final) and according to the Good Laboratory Practices (GLP) published by the French Ministry of Employment and Solidarity (No 2000/5bis, Order of 14 Mar. 2000, JO 23 Mar. 2000).

Study of Subcutaneous Toxicity at 14 Days

The objective of this study was to determine the toxicity of the tobacco leaf extract according to example 1 in rats following subcutaneous administration (once a week for 2 weeks).

The study was conducted as follows:

| Group No | Dose expressed as protein (µg/kg/adm) | Dose volume (mL/kg/adm) | Dose concentration expressed as protein (µg/mL) | Number of animals males | females |
|---|---|---|---|---|---|
| 1 | 0 | 2 | 0 | 6 | 6 |
| 2 | 11.2 | 0.4 | 28 | 6 | 6 |
| 3 | 56 | 2 | 28 | 6 | 6 |

The results of the study showed that:

no mortality is observed at any dose;

no treatment-related clinical signs are observed and subcutaneous administration is well tolerated locally (clinical signs and local tolerance were observed before and after injection, and once daily when no treatment is administered);

the effects on body weight and food consumption (compared to controls) are not harmful;

there are biologically significant differences in white blood cell counts between treated and untreated rodents but these differences have no toxic effect;

variations were observed between the treated and untreated groups in terms of protein and cholesterol concentrations, but these variations remained within or close to those of the control group. These effects are not harmful;

no change was observed in organ weights between the treated group and the control group.

Subcutaneous administration to Wistar rats of the tobacco leaf extract according to example 1 once weekly for 2 weeks at doses of 11.2 and 56 µg protein/kg/adm was therefore well tolerated.

Four-Week Study of Subcutaneous Toxicity

The objective was to determine the toxicity of the tobacco leaf extract according to example 1 following subcutaneous administration once weekly to Wistar rats and to determine the regression of any sign of toxicity over a period of 4 weeks without treatment.

Particular attention was paid to potential immunological phenomena.

| Group/ treatment | Dose[1] (µg/kg/ adm) | Dose volume (mL/kg/ adm) | Dose concentration (µg/mL) | Number of animals | | | |
|---|---|---|---|---|---|---|---|
| | | | | After treatment[2] | | After observation period[3] | |
| | | | | males | females | males | females |
| 1. Control (vehicle: 0.9% NaCl) | 0.0 | 4.0 | 0.0 | 10 | 10 | 5 | 5 |
| 2. low dose | 16.8 | 0.6 | 28.0 | 10 | 10 | / | / |
| 3. intermediate dose | 33.6 | 1.2 | 28.0 | 10 | 10 | / | / |
| 4. high dose | 112.0 | 4.0 | 28.0 | 10 | 10 | 5 | 5 |

[1]Expressed as proteins
[2]Rats killed 2 days after the last administration (day 23)
[3]Rats killed 4 weeks after the last administration (day 49)

During the treatment period, the rats were observed before and at least 3 times after administration. During the observation period, the rats were observed once daily.

A complete clinical examination was performed once a week. Local tolerance was noted before and after each injection, once daily during the first week and then twice weekly until the end of the observation period.

Body temperature was measured the day after each administration (days 1, 8, 15 and 22).

Ophthalmologic examinations were performed before the test, as well as one day after the first and last day of administration (days 1 and 22).

Individual body weights and food consumption were measured twice a week.

Haematological, coagulation, serum clinical chemistry parameter and lymphocyte analyses were performed on days 23 and 49/48 (male/female, respectively). Urine tests were performed on day 23.

All animals were killed 2 days after the last administration or after a 4-week observation period and autopsied. Certain organs were weighed and used for histopathological examinations.

The results of the study showed that:
- no mortality is observed at any dose;
- subcutaneous administration at doses expressed as protein of 16.8, 33.6 and 112.0 µg/kg/adm was well tolerated locally;
- no treatment-related clinical signs are observed;
- body temperature is not affected;
- no treatment-related ophthalmologic effect was observed;
- body weight and food consumption are not affected;
- no significant differences in terms of haematology, coagulation and urine were observed;
- creatine kinase enzyme activity decreased in female groups 3 and 4 (intermediate and high doses; 33.6 and 112 µg/kg/adm, respectively) at the end of the treatment period. These variations were not considered harmful insofar as they are not associated with histopathological features;
- a slight decrease in the number of circulating NK cells in treated females and in males treated with intermediate and high doses (groups 3 and 4);
- at the end of the observation period, the mean number of circulating NK cells in males treated with a high dose (group 4) was lower;
- no change in organ weight was observed;
- a dark spot was observed at the injection site, which corresponds to subcutaneous bleeding during histopathological evaluation. This observation is considered to be unrelated to the administration procedure.

At the end of treatment, minimal or slight inflammatory skin changes were observed at the injection site of groups 3 and 4, while almost no inflammatory change was observed for groups 1 and 2.

At the end of the observation period, the inflammatory changes previously observed for group 4 showed an almost total recovery.

The 4 subcutaneous injections of the tobacco leaf extract according to example 1 up to a dose of 112 µg/kg/adm were well tolerated and only minimal and reversible inflammatory changes occurred in treated rats compared with untreated rats.

In conclusion, under the experimental conditions defined above, subcutaneous administration in Wistar rats of the tobacco leaf extract according to example 1 once weekly for 4 weeks at doses of 16.8, 33.6 and 112 µg/kg/adm was well tolerated and not associated with any adverse effects.

Example 7: Clinical Study Following Administration of a Tobacco Leaf Extract According to Example 1

A pharmaceutical composition comprising the tobacco leaf extract according to example 1, containing 100 µg or 200 µg of proteins and mannitol, was administered by subcutaneous injection a first time on day 0 and a second time on day 29 (1 mL in each arm each time) to 24 smokers. Inclusions were made according to the principle of cohort expansion, 6 initial patients receiving 100 µg being included first, followed by 6 initial patients receiving 200 µg, before the inclusion of 6 additional patients receiving 100 µg. The population of subjects treated consisted of 24 people, 14 men and 10 women, between 30 and 65 years of age with a median age of 44.5 years.

It should be noted that none of the doses tested generated a toxicity of level 3-4 according to the toxicity grades of the Common Terminology Criteria for Adverse Events (CT-CAE) v4.0 of the National Cancer Institute.

The study was conducted as follows:

The initial characteristics of the subjects in terms of tobacco consumption are presented in the table below.

|  | N | % | Median | Range |
| --- | --- | --- | --- | --- |
| Consumer status |  |  |  |  |
| Smoker | 24 | 100 |  |  |
| Consumption |  |  |  |  |
| Manufactured cigarettes, No/day | 18 | 75 | 20 | (15; 30) |
| Rolled cigarettes, No/day | 3 | 12.5 | 20 | (15; 30) |
| Cigarillos, No/day | 3 | 12.5 | 20 | (15; 20) |
| Fagerström dependence level |  |  |  |  |
| 5 | 11 | 46 |  |  |
| 6 | 5 | 21 |  |  |
| 7 | 2 | 8 |  |  |
| 8 | 3 | 12.5 |  |  |
| 9 | 3 | 12.5 |  |  |
| Exhaled CO Measurement (ppm) | 24 |  | 24.5 | (9; 45) |
| Would you like to quit smoking? |  |  |  |  |
| No |  |  |  |  |
| Yes | 24 | 100 |  |  |

Figure 8:
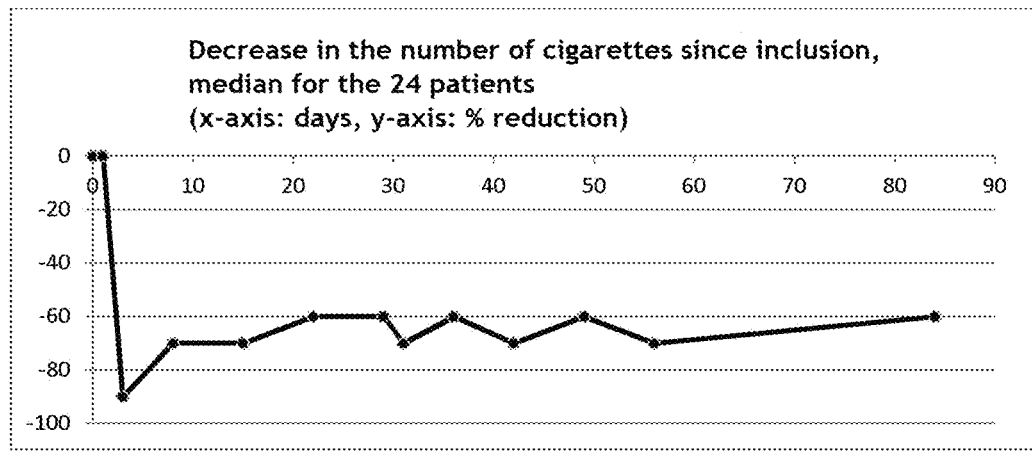
FIGS. 8 and 9. Change in tobacco consumption in patients treated by administration of the tobacco leaf extract according to example 1.
Figure 9:
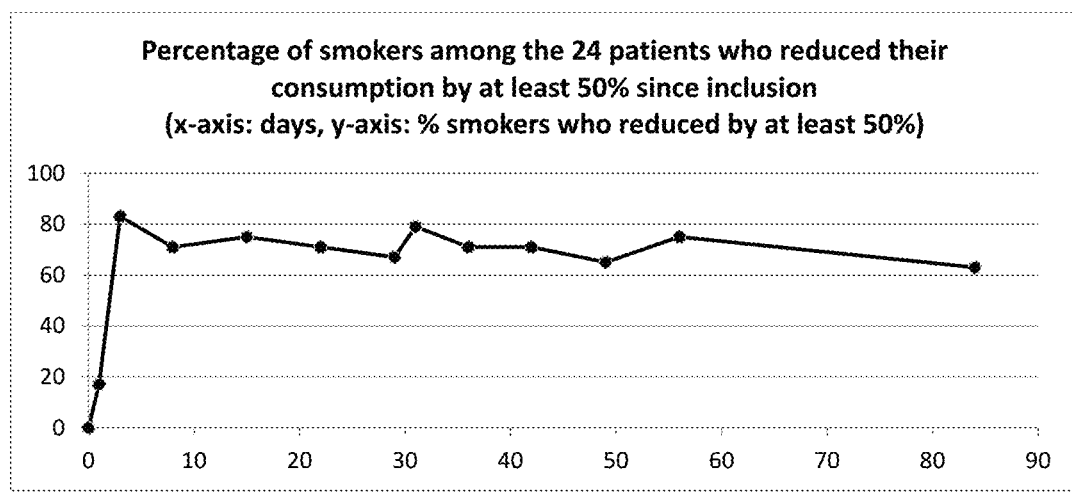

FIGS. 8 and 9 show the evolution of tobacco consumption.

The formula for calculating the decrease in number of cigarettes is as follows: (No of cigarettes visit n−No of cigarettes at inclusion)/No of cigarettes at inclusion.

A point made at 4 weeks showed that 16 smokers (67% of the smokers) had quit smoking or reduced their daily cigarette consumption by at least 50% and that the daily cigarette consumption of the 24 smokers had decreased by 60%.

A point made at 12 weeks showed that 15 smokers (63% of the smokers) had quit smoking or reduced their daily cigarette consumption by at least 50% and that the daily cigarette consumption of the 24 smokers had decreased by 60%.

It is interesting to note that the last 12 smokers (12 out of 24) benefited from a longer delay (sometimes a month or more) between their first contact with the clinical study centre and the injection of a tobacco extract according to example 1, whereas the first 12 smokers had a shorter delay (often only a few days). For these 12 smokers who benefited from a longer delay, the percentage of smokers who reduced their consumption by at least 50% or stopped smoking at 3 and 4 weeks is 83% (10 smokers out of 12) whereas it is 50% (6 smokers out of 12) for the 12 smokers who benefited from a shorter delay. This superior efficacy is explained by the better preparation of those smokers who had more time to reinforce their motivation before receiving an injection of a tobacco extract according to example 1. Of the last 12 smokers, 5 were abstinent continuously from one week after the end of treatment to week 12 (end of follow-up), and 8 were continuously abstinent over the last 7 days at week 12.

The treated smokers describe a reduction in their attraction to cigarettes and their urge to smoke as well as the institution of a certain indifference to cigarettes. They notice a reduction in the palatability of cigarettes. Some speak of a change in the taste of cigarettes. Their motivation to quit is reinforced.

Before administration of the pharmaceutical composition, IgG antibodies directed against the pharmaceutical composition were detected in all patients. Before treatment, the mean concentrations of IgG directed against the pharmaceutical composition were 6.07 microg/ml (standard deviation: 2.98 microg/ml).

After administration of the pharmaceutical composition, a significant increase in concentrations of anti-pharmaceutical composition IgG was observed. Thus, the IgG concentrations measured 29 days after administration of the pharmaceutical composition were 7.19 microg/ml (standard deviation: 4.04 microg/ml) and these concentrations increased to 7.5 microg/ml (standard deviation 4.28 microg/ml) when measured 8 weeks after the first administration of the pharmaceutical composition. Variations in IgG concentrations were significant (t-test significance threshold $p<0.05$) between day 29 and day 0 ($p=0.02$) and between the measurements of week 8 and day 0 ($p=0.006$). A significant difference was also observed between the concentrations of anti-pharmaceutical composition IgG at week 8 and at day 29 ($p=0.029$).

Statistical analysis crossing the concentrations of IgG directed against the pharmaceutical composition and smoking cessation showed correlations (Wilcoxon test, significance threshold $p<0.05$) between higher levels of IgG directed against the pharmaceutical composition and smoking cessation.

Patients who reduced their consumption by at least 50% one week after the first administration of the pharmaceutical composition had higher levels of IgG directed against the pharmaceutical composition at day 29 ($p=0.034$) and at week 8 ($p=0.044$).

Patients who were abstinent for 7 consecutive days (prevalent abstinence) at day 36 had higher levels of IgG directed against the pharmaceutical composition at day 29 ($p<0.001$) and at week 8 ($p<0.001$).

Patients who were abstinent for 7 consecutive days (prevalent abstinence) at week 12 had higher levels of IgG directed against the pharmaceutical composition at day 29 ($p=0.013$) and at week 8 ($p=0.016$).

Patients who were continuously abstinent until week 12 had higher levels of IgG directed against the pharmaceutical composition at day 29 ($p=0.007$) and at week 8 ($p=0.009$).

IgE antibodies were not detected following administration of the pharmaceutical composition.

The invention claimed is:

1. A method for treatment of tobacco addiction comprising administering to a patient in need thereof an effective amount of a tobacco leaf extract or a composition comprising a tobacco leaf extract;
    wherein the tobacco leaf extract contains at least 5% by weight, based on the total weight of the dry extract, of proteins of molecular mass greater than 10 kDa, and is essentially free of molecules of molecular mass less than 10 kDa;
    wherein the content, in the tobacco leaf extract, of proteins whose molecular mass is greater than 500 kDa is less than 15% by weight, based on the total protein weight of the extract.

2. The method for treatment according to claim 1, wherein the proteins are selected from the group consisting of the following protein families: lignin-forming anionic peroxidase, glucan endo-1,3-beta-glucosidase, endochitinase, pathogenesis-related protein, osmotin, proteinase inhibitors, and mixtures thereof.

3. The method for treatment according to claim 1, wherein the content, in the tobacco leaf extract, of proteins whose molecular mass is greater than 100 kDa is less than 15% by weight based on the total protein weight of the extract.

4. The method for treatment according to claim 1, wherein the tobacco leaf extract comprises at least one protein belonging to the family of glucan endo-1,3-beta-glucosidases selected from the group consisting of beta-1,3-endoglucanase acidic isoform PR-Q' (PR36401 according to the UniProt database), beta-1,3-endoglucanase basic vacuolar isoform GLB (P27666 according to the UniProt database), and mixtures thereof.

5. The method for treatment according to claim 1, wherein the tobacco leaf extract comprises at least one protein belonging to the family of endochitinases selected from the group consisting of acidic endochitinase P (P17513 according to the UniProt database), acidic endochitinase Q (P17514 according to the UniProt database), endochitinase B (P24091 according to the UniProt database), and mixtures thereof.

6. The method for treatment according to claim 1, wherein the tobacco leaf extract comprises at least osmotin (P14170 according to the UniProt database).

7. The method for treatment according to claim 1, wherein the tobacco leaf extract comprises at least one lignin-forming anionic peroxidase (P11965 according to the UniProt database).

8. The method for treatment according to claim 1, wherein the tobacco leaf extract comprises at least one pathogenesis-related protein selected from the group consisting of pathogenesis-related protein R (P13046 according to the UniProt database), pathogenesis-related protein PR-4A (PR29062 according to the UniProt database), pathogenesis-related protein PR-4B (PR29063 according to the UniProt database), and mixtures thereof.

9. The method for treatment according to claim 1, wherein the tobacco leaf extract comprises at least one protein belonging to the family of proteinase inhibitors selected from the group consisting of proteinase inhibitor I-B (Q03199 according to the UniProt database), proteinase inhibitor I-A (Q03198 according to the UniProt database), and mixtures thereof.

10. The method for treatment according to claim 1, wherein the protein content in the dry extract of the tobacco leaf extract is at least 10% by weight based on the total weight of the dry extract.

11. The method for treatment according to claim 1, wherein the proteins present in the tobacco leaf extract are present in an amount ranging from 1 to 1 000 µg/mL.

12. The method for treatment according to claim 1, wherein the tobacco leaf extract or the composition is provided in a form suitable for administration by subcutaneous injection, in a form suitable for administration by means of an adhesive transdermal therapeutic system, or in a form suitable for administration by spraying or by vaporization.

13. The method for treatment according to claim 1, wherein the tobacco leaf extract or the composition is provided in a dosage form of 0.03 mL to 10 mL.

14. The method for treatment according to claim 1, wherein the tobacco leaf extract is essentially free of RuBisCO.

* * * * *